US006399628B1

(12) United States Patent
Audia et al.

(10) Patent No.: US 6,399,628 B1
(45) Date of Patent: *Jun. 4, 2002

(54) N-(ARYL/HETEROARYL) AMINO ACID ESTERS, PHARMACEUTICAL COMPOSITIONS COMPRISING SAME, AND METHODS FOR INHIBITING ALPHA- AMYLOID PEPTIDE RELEASE AND/OR ITS SYNTHESIS BY USE OF SUCH COMPOUNDS

(75) Inventors: James E. Audia, Indianapolis, IN (US); Beverly K. Folmer, Newark, DE (US); Varghese John, San Francisco; Lee H. Latimer, Oakland, both of CA (US); Jeffrey S. Nissen, Indianapolis; Jon K. Reel, Carmel, both of IN (US); Eugene D. Thorsett, Moss Beach, CA (US); Celia A. Whitesitt, Greenwood, IN (US)

(73) Assignees: Athena Neurosciences, Inc., San Francisco, CA (US); Eli Lilly & Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/266,908

(22) Filed: Mar. 12, 1999

Related U.S. Application Data

(63) Continuation of application No. 08/975,977, filed on Nov. 21, 1997, now Pat. No. 5,965,614.
(60) Provisional application No. 60/104,593, filed on Nov. 22, 1996.

(51) Int. Cl.[7] .................. C07D 215/38; C07D 277/82; C07D 209/20; C07D 319/14; C07D 317/44; C07D 307/02; C07C 229/28
(52) U.S. Cl. ................. 514/311; 514/367; 514/415; 514/423; 514/452; 514/465; 514/467; 514/471; 514/529; 514/533; 514/538; 514/550; 514/567; 546/171; 548/161; 548/496; 548/540; 549/366; 549/439; 549/451; 549/496; 560/43; 560/45; 560/161; 562/433; 562/457
(58) Field of Search .................. 514/311, 367, 514/413, 423, 452, 465, 467, 471, 529, 533, 538, 550, 567; 546/171; 548/161, 496, 540; 549/366, 439, 451, 496; 560/43, 45, 161; 562/433, 457

(56) References Cited

U.S. PATENT DOCUMENTS

| | | |
|---|---|---|
| 3,598,859 A | 8/1971 | Yates et al. |
| 3,761,508 A | 9/1973 | Haddock |
| 3,882,162 A | 5/1975 | Clayton |
| 3,994,713 A | 11/1976 | Haddock |
| 4,260,782 A | 4/1981 | Grieder et al. |
| 4,267,355 A | 5/1981 | Scott et al. |
| 4,492,683 A | 1/1985 | Nagpal |
| 4,619,685 A | 10/1986 | Kamuro et al. |
| 5,478,857 A | 12/1995 | Clemens et al. |

FOREIGN PATENT DOCUMENTS

| | | |
|---|---|---|
| EP | 0 778 266 | 6/1997 |
| GB | 1 164 160 | 9/1969 |
| GB | 1 289 283 | 9/1972 |
| JP | 51776003 | 7/1982 |
| WO | WO 95/17095 | 6/1995 |
| WO | WO 96/39194 | 12/1996 |

OTHER PUBLICATIONS

Database CAPLUS on STN Acc. No. 1989:595365, Ramamurthy et al., 'Synthesis and antitubercular activity of N–(2–naphthyl) glycine hydrazide analogs.' J. Med. Chem. (1989), 32(11), pp. 2421–6 (abstract), 1989.*

Database CAPLUS on STN, Acc. No. 1991:81891, Ellis et al., 'Preparation of 1–phenyl–1,2,4–triazine–3,5–(2H,4H) diones as 5–lipoxygenase inhibitors.' EP 388165 (abstract) 1991.*

Database CALUS on STN, Acc. No. 1983:102691, Mitsui toatsu Chemicals, Inc., 'Phenylamino acid derivatives as herbicides.' JP 57116003 (abstract), 1983.*

Chemical Abstracts, vol. 54, No. 11, Jun. 10, 1960.

Cordell, β–Amyloid Formation as a Potential Therapeutic Target for Alzheimer's Disease, Annu. Rev. Pharmacol. Toxicol. 34:69–89 (1994).

Database CAPLUS on STN, Doc. No. 105:153498, Pirkle et al., 'Chromatographic separation of the enantiomers of 2–carboalkoxyindolines and N–aryl–alpha–amono esters on chiral stationary phases derived from N–(3,5)–dinitrobenzoyl)–alpha–amino acids.' Abstract.

Database CAPLUS on STN, Doc. No. 110:57616, Previtera et al., 'N,N'–substituted piperazine–2,5–dones. III. Synthesis and pharmacological activities of some 1–aryl–4= arylidene (or heteroarylidene) aminopeperazine–2,5–dione derivatives.' Abstract of Farmac.

(List continued on next page.)

Primary Examiner—Sreeni Padmanabhan
Assistant Examiner—Brian J. Davis
(74) Attorney, Agent, or Firm—Burns, Doane, Swecker & Mathis LLP

(57) ABSTRACT

Disclosed are compounds which inhibit β-amyloid peptide release and/or its synthesis, and, accordingly, have utility in treating Alzheimer's disease. Also disclosed are pharmaceutical compositions comprising a compound which inhibits β-amyloid peptide release and/or its synthesis as well as methods for treating Alzheimer's disease both prophylactically and therapeutically with such pharmaceutical compositions.

20 Claims, No Drawings

OTHER PUBLICATIONS

Database CAPLUS on STN, Doc. No. 112:198426, Waterhouse, et al., 'Preparation and formulation of dihydro–4–methyl–1–phenyl–1,2,4–triazine–3,5–(2H, 4H)–diones as 5–lipoxygenase inhibitors.' Abstract of EP 340030 A2.

Database CAPLUS on STN, Doc. No. 116:189639, Weber et al., 'Synergistic insecticidal compositions comprising phenylalanine esters.' abstract of DD 295524 A5.

DeVries, Vern G., et al., "Potential antiatherosclerotic agents.4.'(Functionalized– alkyl) amino acid analogs of cetaben", *J. Med. Chem.*, 26 (10):1411–21 (1983).

Hyun, Myung Ho, et al., "A new chiral stationary phase bearing both.pi.–acidic and.pi.–basic sites derived from (S)–tyrosine for the liquid chromatographic resolution of racemates", *Chem. Lett.*, (8):1463–6 (1994).

Kamuro, et al., Chem. Abstracts 106:28836h (1987).

Ogawa, et al., A New Method for Preparing D–Penicillamine. Reaction of Benzylpenicilloic Acid α–Amides with Arylamines, Chem. Pharm. Bull., 36(6):1957–1962 (1988).

Patent Abstracts of Japan, vol. 006, No. 208 (C–130), Oct. 20, 1982—& JP 57 116003 A (Mitsui Toatsu Kagaku KK), Jul. 19, 1982.

Pirkle, WIlliam H., et al., "Chromatographic separation of the enantiomers of 2–carboalkoxyindolines and N–aryl–alpha.–amino esters on chiral stationary phases derived from N–(3,5–dinitrobenzoyl)–.alpha.–amino acids", *J. Chromatogr.*, 348 (1):89–96 (1985).

Pirkle, William H., et al., "Preparation of N–(2–naphthyl)–2–amino acids and esters of high enantiomeric purity", *J. Org. Chem.*, 51 (1):102–5 (1986).

Pirkle, William H., et al., "An investigation into the role of solvation in a well characterized chiral recognition system", *J. Liq. Chromatogr.*, 14(11):2027–42 (1991).

Ramamurthy, B., et al., "Synthesis and antitubercular activity of N–(2–naphthyl) glycine hydrazide analogs", *J. Med. Chem.*, 32 (11):2421–6 (1989).

Smith, et al., β–APP Processing as a Therapeutic Target for Alzheimer's Disease, Current Pharmaceutical Design, 3 439–445 (1997).

\* cited by examiner

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 43 amino acids
      (B) TYPE: peptide
      (D) TOPOLOGY: linear (ii) MOLECULE TYPE: peptide (xi) SEQUENCE DESCRIPTION: SEQ ID NO 1:

Asp Ala Glu Phe Arg His Asp Ser Gly Tyr Glu Val His His Gln Lys
1               5                   10                  15

```
                                        -continued
Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```

N-(ARYL/HETEROARYL) AMINO ACID ESTERS, PHARMACEUTICAL COMPOSITIONS COMPRISING SAME, AND METHODS FOR INHIBITING ALPHA- AMYLOID PEPTIDE RELEASE AND/OR ITS SYNTHESIS BY USE OF SUCH COMPOUNDS

CROSS-REFERENCE TO RELATED APPLICATIONS

This application is a continuation of application No. 08/975,977, filed Nov. 21, 1997, now U.S. Pat. No. 5,965,614, which claims the benefit of provisional Application No. 60/104,593, filed Nov. 22, 1996, which was converted pursuant to 37 C.F.R. §1.53(b)(2)(ii) from U.S. patent application No. 08/755,444, filed Nov. 22, 1996.

BACKGROUND OF THE INVENTION

FIELD OF THE INVENTION

This invention relates to compounds which inhibit β-amnyloid peptide release and/or its synthesis, and, accordingly, have utility in treating Alzheimer's disease.

REFERENCES

The following publications, patents and patent applications are cited in this application as superscript numbers:

1 Glenner, et al., "Alzheimier's Disease: Initial Report of the Purification and Characterization of a Novel Cerebrovascular Amyloid Protein", *Biochem. Biophys. Res. Commun.,* 120:885–890 (1984).

2 Glenner, et al., "Polypeptide Marker for Alzheimner's Disease and its Use for Diagnosis", U.S. Pat. No. 4,666,829 issued May 19, 1987.

3 Selkoe, "The Molecular Pathology of Alzheimer's Disease", *Neuron,* 6:487–498 (1991).

4 Goate, et al., "Segregation of a Missense Mutation in the Amyloid Precursor Protein Gene with Familial Alzheimer's Disease", *Nature,* 349:704–706 (1990).

5 Chartier-Harlan, et al., "Early-Onset Alzheimer's Disease Caused by Mutations at Codon 717 of the β-Amyloid Precursor Proteing Gene", *Nature,* 353:844–846 (1989).

6 Murrell, et al., "A Mutation in the Amyloid Precursor Protein Associated with Hereditary Alzheimer's Disease", *Science,* 254:97–99 (1991).

7 Mullan, et al., "A Pathogenic Mutation for Probable Alzheimer's Disease in the APP Gene at the N-Terminus of β-Amyloid, *Nature Genet.,* 1:345–347 (1992).

8 Schenk, et al., "Methods and Compositions for the Detection of Soluble β-Amyloid Peptide", International Patent Application Publication No. WO 94/10569, published May 11, 1994.

9 Selkoe, "Amyloid Protein and Alzheimer's Disease", *Scientific American,* pp. 2–8, November, 1991.

10 Yates, et al., "N,N-Disubstituted Amino Acid Herbicides", U.S. Pat. No. 3,598,859, issued Aug. 10, 1971.

11 Losse, et al., Tetrahedron, 27:1423–1434 (1971).

12 Citron, et al., "Mutation of the β-Amyloid Precursor Protein in Familial Alzheimer's Disease Increases β-Protein Production, *Nature,* 360:672–674 (1992).

13 Hansen, et al., "Reexamination and Further Development of a Precise and Rapid Dye Method for Measuring Cell Growth/Cell Kill", *J. Immun. Meth.,* 119:203–210 (1989).

All of the above publications, patents and patent applications are herein incorporated by reference in their entirety to the same extent as if each individual publication, patent or patent application was specifically and individually indicated to be incorporated by reference in its entirety.

STATE OF THE ART

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein (APP), that is normally produced by cells in many tissues of various animals, including humans. Knowledge of the structure of the gene encoding the APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition. The class of compounds having the described properties are defined by formula I below:

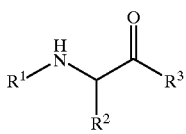

I wherein
$R^1$ is selected from the group consisting of:
(a) a substituted phenyl group of formula II:

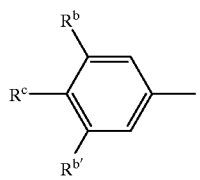

II wherein
$R^c$ is selected from the group consisting of acyl, alky, alkoxy, alkoxycarbonyl, alkylalkoxy, azido, cyano, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
$R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
(b) 2-naphthyl; and
(c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;
$R^2$ is selected from the group consisting of hydrogen, alkyl of from 1 to 4 carbon atoms, alkylalkoxy of from 1 to 4 carbon atoms and alkylthioalkoxy of from 1 to 4 carbon atoms; and
$R^3$ is selected from the group consisting of:
(a) —Y(CH$_2$)$_n$CHR$^4$R$^5$ wherein n is an integer of from 0 to 2, Y is selected from the group consisting of oxygen and sulfur, $R^4$ and $R^5$ are independently selected from the group consisting of hydrogen, alkyl, alkenyl, aryl optionally substituted with from 1 to 3 substituents selected from the group consisting of alkyl, alkoxy, halo, cyano, nitro, trihalomethyl, and thioalkoxy, heteroaryl optionally substituted with from 1 to 3 substituents selected from the group consisting of alkyl, alkoxy, halo, cyano, nitro, trihalomethyl, and thioalkoxy, and where $R^4$ and $R^5$ are joined to form a cycloalkyl group, a cycloalkenyl group, or a heterocyclic group;
(b) —ON=C(NH$_2$)R$^6$ where $R^6$ is selected from the group consisting of alkyl, aryl, cycloalkyl, and heteroaryl;
(c) —O(CH$_2$)$_p$C(O)OR$^7$ wherein p is an integer of from 1 to 2 and $R^7$ is alkyl;
(d) —NR$^8$R$^9$ wherein $R^8$ and $R^9$ are joined to form a pyrrolyl group; and
pharmaceutically acceptable salts thereof
with the provisos that
1. when $R^1$ is the substituted phenyl group of formula II above, $R^{b'}$ is hydrogen, $R^b$ and $R^c$ are chloro, and $R^2$ is methyl, then $R^3$ is not —OCH(CH$_3$)-φ;
2. when $R^1$ is the substituted phenyl group of formula II above, when $R^{b'}$ is hydrogen, $R^b$ and $R^c$ are chloro, and $R^3$ is —OCH$_2$CH$_3$ then $R^2$ is not hydrogen;
3. when $R^1$ is the substituted phenyl group of formula II above, $R^{b'}$ is hydrogen, $R^b$ and $R^c$ are chloro, and $R^3$ is —OCH$_2$CH(CH$_3$)$_2$ then $R^2$ is not —CH(CH$_3$)CH$_2$CH$_3$; and
4. when $R^1$ is N-methylindol-5-yl and $R^2$ is methyl, then $R^3$ is not —OCH$_2$CH$_3$.

Surprisingly, any substituents at the 2 and/or 6 positions or substituents at the 3, 4 and/or 5 positions, other than those specifically specified above, eliminate the ability of the resulting compounds to inhibit β-amyloid peptide release and/or its synthesis.

Accordingly, in one of its method aspects, this invention is directed to a method for inhibiting β-amyloid peptide release and/or its synthesis in a cell which method comprises administering to such a cell an amount of a compound or a mixture of compounds of formula I above effective in inhibiting the cellular release and/or synthesis of β-amyloid peptide.

Because the in vivo generation of β-amyloid peptide is associated with the pathogenesis of AD[8,9], the compounds of formula I can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD which method comprises administering to said patient a pharmaceutical composition comprising a pharmaceutically inert carrier and an effective amount of a compound or a mixture of compounds of formula I above.

In yet another of its method aspects, this invention is directed to a therapeutic method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I above.

In formula I above, $R^1$ substituted phenyls are preferably 4-substituted, 3,5-disubstituted or 3,4-disubstituted phenyl substituents wherein the substituents at the 3 and/or 5 positions are defined by $R^b$, $R^{b'}$ as above and the substituent at the 4 position is defined by $R^c$ as above. Particularly preferred 3,5-disubstituted phenyls include, by way of example, 3,5-dichlorophenyl, 3,5-difluorophenyl, 3,5-di(trifluoromethyl)phenyl, 3,5-dimethoxyphenyl, and the like. Particularly, preferred 3,4-disubstituted phenyls include, by way of example, 3,4-dichlorophenyl, 3,4-difluorophenyl, 3-(trifluoromethyl)-4-chlorophenyl, 3-chloro-4-cyanophenyl, 3-chloro-4-iodophenyl, 3,4-methylenedioxyphenyl, 3,4-ethylenedioxyphenyl, and the like. Particularly preferred 4-substituted phenyls include, by way of example, 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, 4-(1-ethoxy)ethylphenyl, 4-(ethoxycarbonyl)phenyl, and the like.

Other preferred $R^1$ substituents include, by way of example, 2-naphthyl, 2-methylquinolin-6-yl, benzothiazol-6-yl, 5-indolyl, and the like.

Preferably $R^2$ is selected from the group consisting of alkyl of from 1 to 4 carbon atoms, alkylalkoxy of from 1 to 4 carbon atoms and alkylthioalkoxy of from 1 to 4 carbon atoms. Particularly preferred $R^2$ substituents include, by way of example, methyl, ethyl, n-propyl, iso-butyl, and the like.

Preferred $R^3$ substituents include methoxy, ethoxy, iso-propoxy, n-propoxy, n-butoxy, iso-butoxy, cyclopentoxy, allyloxy, 4-methylpentoxy, —O—$CH_2$-(2,2-dimethyl-1,3-dioxolan-4-yl), —O—$CH_2$-cyclohexyl, —O—$CH_2$-(3-tetrahydrofuranyl), —O—$CH_2$—C(O)O-tert-butyl, —O—$CH_2$—C($CH_3$)$_3$, —O—$CH_2$-φ, —O$CH_2$CH($CH_2CH_3$)$_2$, —O($CH_2$)$_3$CH($CH_3$)$_2$, —ON=C($NH_2$)φ, —ON=C($NH_2$)$CH_3$, —ON=C($NH_2$)$CH_2CH_3$, —ON=C($NH_2$)$CH_2CH_2CH_3$, —ON=C($NH_2$)-cyclopropyl, —ON=C($NH_2$)—$CH_2$-cyclopropyl, —ON=C($NH_2$)-cyclopentyl, —ON=C($NH_2$)$CH_2$CH($CH_3$)$_2$, and the like.

This invention also provides for novel pharmaceutical compositions comprising a pharmaceutically inert carrier and a compound of the formula I above.

Particularly preferred compounds for use in the methods and compositions of this invention include, by way of example, the following wherein the stereochemistry of the $R^2$ group (where appropriate) is derived from the L-amino acid:

N-(3,4-dichlorophenyl)alanine ethyl ester;
N-(3-trifluoromethyl-4-chlorophenyl)alanine ethyl ester;
N-(3,5-dichlorophenyl)alanine ethyl ester;
N-(3,4-difluorophenyl)alanine ethyl ester;
N-(3,4-dichlorophenyl)alanine benzyl ester;
N-(3,4-dichlorophenyl)alanine iso-butyl ester;
N-(3,4-dichlorophenyl)alanine iso-propyl ester;
N-(3,4-dichlorophenyl)alanine n-butyl ester;
N-(3,4-dichlorophenyl)alanine methyl ester;
N-(3,4-dichlorophenyl)alanine cyclopentyl ester;
N-(3,4-dichlorophenyl)alanine n-propyl ester;
N-(3,4-dichlorophenyl)alanine allyl ester;
N-(3,4-dichlorophenyl)alanine 4-methylpentyl ester;
N-(3,4-dichlorophenyl)alanine 2,2-dimethyl-1,3-dioxolane-4-methyl ester;
N-(3,4-dichlorophenyl)alanine cyclohexylmethyl ester;
N-(3,4-dichlorophenyl)alanine tert-butoxycarbonylmethyl ester;
N-(3,4-dichlorophenyl)leucine iso-butyl ester;
2-[N-(3,4-dichlorophenyl)amino]pentanoic acid iso-butyl ester;
N-(4-cyanophenyl)alanine iso-butyl ester;
N-(3-chloro-4-cyanophenyl)alanine iso-butyl ester;
N-(3,4-dichlorophenyl)alanine tetrahydrofuran-3-yl-methyl ester;
N-(3-chloro-4-iodophenyl)alanine iso-butyl ester;
2-[N-(3,4-dichlorophenyl)amino]butanoic acid isobutyl ester;
N-(4-chlorophenyl)alanine iso-butyl ester;
N-(3,5-dichlorophenyl)alanine iso-butyl ester;
N-(4-ethylphenyl)alanine methyl ester;
N-[4-(1-ethoxy)ethylphenyl]alanine methyl ester;
N-(3,4-dichlorophenyl)alanine 2,2-dimethylpropyl ester;
N-(3,4-dichlorophenyl)glycine iso-butyl ester;
N-(3,4-dichlorophenyl)alanine 2-ethylbutyl ester;
N-(3-chloro-4-iodophenyl)alanine iso-butyl ester;
N-(4-azidophenyl)alanine iso-butyl ester;
N-[(4-phenylcarbonyl)phenyl]alanine iso-butyl ester;
N-(3,5-difluorophenyl)alanine iso-butyl ester;
N-(3,4-dichlorophenyl)alanine O-acylacetamidoxime ester,
N-(3,4-dichlorophenyl)alanine pyrrolyl amide;
N-(3,4-dichlorophenyl)alanine O-acylpropionamideoxime ester;
N-(3,4-dichlorophenyl)alanine O-acylbutyramideoxime ester;
2-[N-(naphth-2-yl)amino]butanoic acid ethyl ester;
N-(naphth-2-yl)alanine iso-butyl ester;
N-(2-methylquinolin-6-yl)alanine iso-butyl ester;
N-(3,4-ethylenedioxyphenyl)alanine iso-butyl ester;
N-(3,4-methylenedioxyphenyl)alanine iso-butyl ester;
N-(naphth-2-yl)alanine methyl ester;
N-(benzothiazol-6-yl)alanine ethyl ester;
N-(indol-5-yl)alanine iso-butyl ester;
N-(naphth-2-yl)alanine O-acylacetamidoxime ester;
N-(2-naphthyl)alanine ethyl ester;
N-(4-ethoxycarbonylphenyl)alanine iso-butyl ester;
N-(3,5-di(trifluoromethyl)phenyl)alanine iso-butyl ester;
N-(3,5-dimethoxyphenyl)alanine iso-butyl ester;
N-(2-napthyl)alanine O-acylpropionamidoxime ester;
N-(2-napthyl)alanine O-acylbutyramidoxime ester;
N-(2-napthyl)alanine O-acylisovaleramidoxie ester;
N-(2-napthyl)alanine O-acylbenzamidoxime ester;
N-(2-napthyl)alanine O-acylcyclopropanecarboxamidoxime ester;
N-(2-napthyl)alanine O-acylcyclopropylacetamidoxime ester; and
N-(2-napthyl)alanine O-acylcyclopentanecarboxamidoxime ester.

Still further, this invention provides for novel compounds of the formula III:

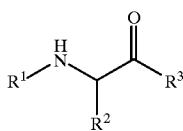

wherein
R¹ is selected from the group consisting of:
(a) a substituted phenyl group of formula II:

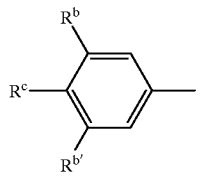

wherein
$R^c$ is selected from the group consisting of acyl, alkyl, alkoxy, alkoxycarbonyl, alkylalkoxy, azido, cyano, halo, hydrogen, nitro, trihalomethyl, thioalkoxy, and where $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
$R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
(b) 2-naphthyl; and
(c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;
$R^2$ is selected from the group consisting of hydrogen, alkyl of from 1 to 4 carbon atoms, alkylalkoxy of from 1 to 4 carbon atoms and alkylthioalkoxy of from 1 to 4 carbon atoms; and
$R^3$ is selected from the group consisting of:
(a) $-Y(CH_2)_nCHR^4R^5$ wherein n is an integer of from 0 to 2, Y is selected from the group consisting of oxygen and sulfur, $R^4$ and $R^5$ are independently selected from the group consisting of hydrogen, alkyl, alkenyl, aryl optionally substituted with from 1 to 3 substituents selected from the group consisting of alkyl, alkoxy, halo, cyano, nitro, trihalomethyl, and thioalkoxy, heteroaryl optionally substituted with from 1 to 3 substituents selected from the group consisting of alkyl, alkoxy, halo, cyano, nitro, trihalomethyl, and thioalkoxy, and where $R^4$ and $R^5$ are joined to form a cycloalkyl group, a cycloalkenyl group or a heterocyclic group;
(b) $-ON=C(NH_2)R^6$ where $R^6$ is selected from the group consisting of alkyl, aryl, cycloalkyl, and heteroaryl;
(c) $-O(CH_2)_pC(O)OR^7$ wherein p is an integer of from 1 to 2 and $R^8$ is alkyl; and
(d) $-NR^8R^9$ wherein $R^8$ and $R^9$ are joined to form a pyrrolyl group;

and pharmaceutically acceptable salts thereof
with the proviso excluding the following compounds:

1. when $R^1$ is the substituted phenyl group of formula II above, $R^{b'}$ is hydrogen, $R^b$ and $R^c$ are chloro, and $R^2$ is methyl, then $R^3$ is not $-OCH(CH_3)$-φ;
2. when $R^1$ is the substituted phenyl group of formula II above, when $R^{b'}$ is hydrogen, $R^b$ and $R^c$ are chloro, and $R^3$ is $-OCH_2CH_3$ then $R^2$ is not hydrogen;
3. when $R^1$ is the substituted phenyl group of formula II above, $R^{b'}$ is hydrogen, $R^b$ and $R^c$ are chloro, and $R^3$ is $-OCH_2CH(CH_3)_2$ then $R^2$ is not $-CH(CH_3)CH_2CH_3$; and
4. when $R^1$ is N-methylindol-5-yl and $R^2$ is methyl, then $R^3$ is not $-OCH_2CH_3$;

and still with further proviso excluding the following known compounds: N-(4-chlorophenyl)alanine ethyl ester; N-(3,4-dichlorophenyl)alanine ethyl ester; N-(3,5-dichlorophenyl)alanine ethyl ester; N-(4-n-butylphenyl)alanine ethyl ester; N-(3,4-dinitrophenyl)alanine ethyl ester; N-(4-chlorophenyl)glycine heptenyl ester; N-(4-methylphenyl)glycine butyl ester; N-(3-nitrophenyl)glycine decyl ester; N-(3,4-difluorophenyl)alanine methyl ester; N-(3,4difluorophenyl)alanine ethyl ester; N-(3,4-difluorophenyl)alanine iso-propyl ester; N-(4-fluorophenyl)alanine ethyl ester; N-(3-chloro-4-fluorophenyl)alanine methyl ester; N-(3-chloro-4-fluorophenyl)alanine ethyl ester; and N-(3-chloro-4-fluorophenyl)alanine iso-propyl ester.

Preferred compounds of formula I above include those set forth in Formula IV below:

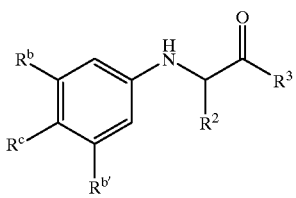

| $R^b$ | $R^c$ | $R^{b'}$ | $R^2$ | $R^3$ |
|---|---|---|---|---|
| $-CF_3$ | $-Cl$ | H | $-CH_3$ | $-OCH_2CH_3$ |
| $-Cl$ | $-Cl$ | H | $-CH_3$ | $-OCH_2CH_3$ |
| $-Cl$ | $-Cl$ | H | $-CH_3$ | $-OCH_2$-φ |

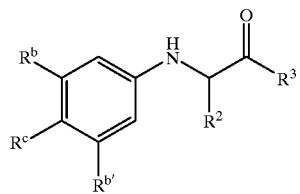

IV

| $R^b$ | $R^c$ | $R^{b'}$ | $R^2$ | $R^3$ |
|---|---|---|---|---|
| —Cl | —Cl | H | —CH₃ | —OCH₂CH(CH₃)₂ |
| —Cl | —Cl | H | —CH₃ | —OCH(CH₃)₂ |
| —Cl | —Cl | H | —CH₃ | —O(CH₂)₃CH₃ |
| —Cl | —Cl | H | —CH₃ | —OCH₃ |
| —Cl | —Cl | H | —CH₃ | —O-cyclopentyl |
| —Cl | —Cl | H | —CH₃ | —OCH₂CH₂CH₃ |
| —Cl | —Cl | H | —CH₃ | —O-allyl |
| —Cl | —Cl | H | —CH₃ | —O(CH₂)₃CH(CH₃)₂ |
| —Cl | —Cl | H | —CH₃ | —O—CH₂-(2,2-dimethyl-1,3-dioxolan-4-yl) |
| —Cl | —Cl | H | —CH₃ | —OCH₂-cyclohexyl |
| —Cl | —Cl | H | —CH₃ | —OCH₂C(O)O-tert-butyl |
| —Cl | —Cl | H | —CH₂CH(CH₃)₂ | —OCH₂CH(CH₃)₂ |
| —Cl | —Cl | H | —CH₂CH₂CH₃ | —OCH₂CH(CH₃)₂ |
| H | —CN | H | —CH₃ | —OCH₂CH(CH₃)₂ |
| —Cl | —CN | H | —CH₃ | —OCH₂CH(CH₃)₂ |
| —Cl | —Cl | H | —CH₃ | —OCH₂CH(CH₃)₂ |
| —Cl | —Cl | H | —CH₃ | —OCH₂-(3-tetra-hydrofuranyl) |
| —Cl | —I | H | —CH₃ | —OCH₂CH(CH₃)₂ |
| —Cl | —Cl | H | —CH₂CH₃ | —OCH₂CH(CH₃)₂ |
| H | —Cl | H | —CH₃ | —OCH₂CH(CH₃)₂ |
| —Cl | H | —Cl | —CH₃ | —OCH₂CH(CH₃)₂ |
| H | —CH₂CH₃ | H | —CH₃ | —OCH₃ |
| H | —CH(CH₃)—OC₂H₅ | H | —CH₃ | —OCH₃ |
| —Cl | —Cl | H | —CH₃ | —OCH₂C(CH₃)₄ |
| —Cl | —Cl | H | —H | —OCH₂CH(CH₃)₂ |
| —Cl | —Cl | H | —CH₃ | —OCH₂CH(CH₂CH₃)₂ |
| —Cl | —I | H | —CH₃ | —OCH₂CH(CH₃)₂ |
| H | azido | H | —CH₃ | —OCH₂CH(CH₃)₂ |
| H | —C(O)φ | H | —CH₃ | —OCH₂CH(CH₃)₂ |
| —F | H | —F | —CH₃ | —OCH₂CH(CH₃)₂ |
| —Cl | —Cl | H | —CH₃ | —O—N=C(NH₂)CH₃ |
| —Cl | —Cl | H | —CH₃ | N-pyrrolyl |
| H | —CO₂CH₂CH₃ | H | —CH₃ | —OCH₂CH(CH₃)₂ |
| —CF₃ | H | —CF₃ | —CH₃ | —OCH₂CH(CH₃)₂ |
| —Cl | —Cl | H | —CH₃ | —ON=C(NH₂)—CH₂CH₃ |
| —Cl | —Cl | H | —CH₃ | —ON=C(NH₂)—CH₂CH₂CH₃ |
| —OCH₃ | H | —OCH₃ | —CH₃ | —OCH₂CH(CH₃)₂ |

Other preferred compounds of formula I include those set forth in the following formula V:

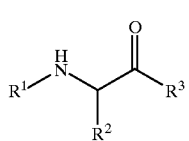

V

| $R^1$ | $R^2$ | $R^3$ |
|---|---|---|
| 2-naphthyl | —CH₂CH₃ | —OCH₂CH₃ |
| 2-naphthyl | —CH₃ | —OCH₂CH(CH₃)₂ |
| 2-methylquinolin-3-yl | —CH₃ | —OCH₂CH(CH₃)₂ |
| 3,4-ethylene-dioxyphenyl | —CH₃ | —OCH₂CH(CH₃)₂ |
| 3,4-methylene-dioxyphenyl | —CH₃ | —OCH₂CH(CH₃)₂ |
| 2-naphthyl | —CH₃ | —OCH₃ |

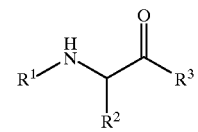

V

| $R^1$ | $R^2$ | $R^3$ |
|---|---|---|
| benzothiazol-6-yl | —CH₃ | —OCH₂CH₃ |
| 5-indolyl | —CH₃ | —OCH₂CH(CH₃)₂ |
| 2-naphthyl | —CH₃ | —O—N=C(NH₂)CH₃ |
| 2-naphthyl | —CH₃ | —OCH₂CH₃ |
| 2-naphthyl | —CH₃ | —O—N=C(NH₂)CH₂CH₃ |
| 2-naphthyl | —CH₃ | —O—N=C(NH₂)CH₂CH₂CH₃ |
| 2-naphthyl | —CH₃ | —O—N=C(NH₂)CH₂CH(CH₃)₂ |

-continued

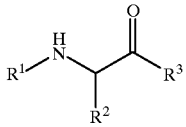

V

| R¹ | R² | R³ |
|---|---|---|
| 2-naphthyl | —CH₃ | —O—N=C(NH₂)φ |
| 2-naphthyl | —CH₃ | —O—N=C(NH₂)-cyclopropyl |
| 2-naphthyl | —CH₃ | —O—N=C(NH₂)CH₂-cyclopropyl |
| 2-naphthyl | —CH₃ | —O—N=C(NH₂)-cyclopentyl |

DETAILED DESCRIPTION OF THE INVENTION

As above, this invention relates to compounds which inhibit β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is approximately a 39–43 amino acid fragment of a large membrane-spanning glycoprotein, referred to as the β-amyloid precursor protein (APP). Its 43-amino acid sequence is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr (SEQ ID NO: 1)
or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

"Alkylene" refers to divalent alkylene groups preferably having from 1 to 10 carbon atoms and more preferably 1 to 6 carbon atoms. This term is exemplified by groups such as methylene (—CH₂—), ethylene (—CH₂CH₂—), the propylene isomers (e.g., —CH₂CH₂CH₂— and —CH(CH₃) CH₂—) and the like.

"Alkaryl" refers to -alkylene-aryl groups preferably having from 1 to 10 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O—" where alkyl is as defined herein. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxycarbonyl" refers to the group "alkyl-O—C(O)—" wherein alkyl is as defined herein. Such groups include, by way of example, methoxycarbonyl, ethoxycarbonyl, n-propoxycarbonyl, iso-propoxycarbonyl, n-butoxycarbonyl, tert-butoxyfarbonyl, sec-butoxycarbonyl, n-pentoxycarbonyl, n-hexoxycarbonyl, and the like.

"Alkylalkoxy" refers to the group "-alklene-O-alkyl" wherein alkylene and alkoxy are as defined herein. Such groups include, by way of example, methyl methoxy (—CH₂OCH₃), ethyl methoxy (—CH₂CH₂OCH₃), n-propyl-iso-propoxy (—CH₂CH₂CH₂OCH(CH₃)₂), methyl-tert-butoxy (—CH₂—O—C(CH₃)₃) and the like.

"Alkylthioalkoxy" refers to the group "-alkylene-S-alkyl" wherein alkylene and alkoxy are as defined herein. Such groups include, by way of example, methylthiomethoxy (—CH₂SCH₃), ethylthiomethoxy (—CH₂CH₂SCH₃), n-propyl-iso-thiopropoxy (—CH₂CH₂CH₂SCH(CH₃)₂), methyl-tert-thiobutoxy (—CH₂SC(CH₃)₃) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH₂), n-propenyl (—CH₂CH=CH₂), iso-propenyl (—C(CH₃)=CH₂), but-2-enyl (—CH₂CH=CHCH₃) and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH₂C≡CH) and the like.

"Acyl" refers to the groups alkyl-C(O)—, aryl-C(O)—, and heteroaryl-C(O)— where alkyl, aryl and heteroaryl are as defined herein.

"Acylamino" refers to the group —C(O)NRR where each R is independently hydrogen or alkyl where alkyl is as defined herein.

"Aminoacyl" refers to the group —NRC(O)R where each R is independently hydrogen or alkyl where alkyl is as defined herein.

"Acyloxy" refers to the groups alkyl-C(O)O—, aryl-C(O)O—, heteroaryl-C(O)O—, and heterocyclic-C(O)O— where alkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, alkoxy, alkenyl, alkynyl, amino, aminoacyl, aryl, aryloxy, carboxyl, alkoxycarbonyl, acylamino, cyano, halo, nitro, heteroaryl, trihalomethyl and the like. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Halo" or "halogen" refers to fluoro, chloro, bromo and iodo and preferably is either chloro or fluoro.

"Heteroaryl" refers to a monovalent aromatic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heterocyclic groups can have a single ring (e.g., piperidinyl or tetrahydrofuryl) or multiple condensed rings (e.g., indolinyl, dihydrobenzoftu or quinuclidinyl). Preferred heterocycles include piperidinyl, pyrrolidinyl and tetrahydrofiiryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

In the compounds of formula I, $R^b$ and $R^c$ can be fused to form a heteroaryl or heterocyclic ring with the phenyl ring. Fusion in this manner results in a fused bicyclic ring structure of the formula:

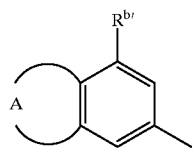

where $R^{b'}$ is as defined above and A is the fused heteroaryl or heterocyclic group containing from 3 to 8 atoms of which from 1 to 3 are heteroatoms independently selected from the group consisting of oxygen, nitrogen and sulfur wherein the two atoms of the phenyl ring are included in the total atoms present in the heteroaryl or heterocyclic group. Examples of such fused ring systems include, for instance, indol-5-yl, indol-6-yl, thionaphthen-5-yl, thionaphthen-6-yl, isothionaphthen-5-yl, isothionaphthen-6-yl, indoxazin-5-yl, indoxazin-6-yl, benzoxazol-5-yl, benzoxazol-6-yl, anthranil-5-yl, anthranil-6-yl, quinolin-6-yl, quinolin-7-yl, isoquinolin-6-yl, isoquinolin-7-yl, cinnolin-6-yl, cinnolin-7-yl, quinazolin-6-yl, quinazolin-7-yl, benzofuran-5-yl, benzofuran-6-yl, isobenzofuran-5-yl, isobenzofuran-6-yl, and the like.

"Thiol" refers to the group —SH.

"Thioalkoxy" refers to the group —S-alkyl.

"Thioaryloxy" refers to the group aryl-S— wherein the aryl group is as defined above including optionally substituted aryl groups as also defined above.

"Thioheteroaryloxy" refers to the group heteroaryl-S— wherein the heteroaryl group is as defined above including optionally substituted aryl groups as also defined above.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of formula I above are readily prepared via several divergent synthetic routes with the particular route selected relative to the ease of compound preparation, the commercial availability of starting materials, and the like.

A first synthetic method involves conventional coupling of a halo acetic acid with a primary amine to form the amino acid followed by conventional esterification as shown in reaction (1) below:

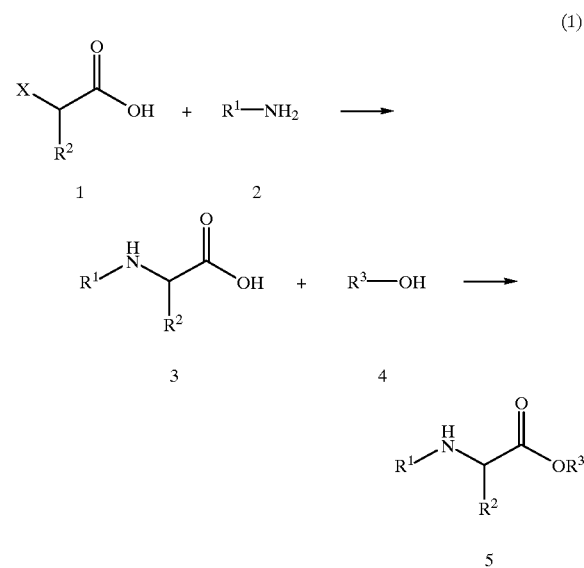

wherein $R^1$, $R^2$, $R^3$ are as defined above and X is a halo group such as chloro or bromo. Alternatively, leaving groups other than halo may be employed such as triflate, tosylate, mesylate and the like. Additionally, a suitable ester of 1 may be employed in this reaction.

The first step of reaction (1) involves coupling of a suitable haloacetic acid derivative 1 with a primary aryl/heteroarylamine 2 under conditions which provide for amino acid 3. This reaction is described by, for example, Yates, et al.[10] and proceeds by combining approximately stoichiometric equivalents of haloacetic acid 1 with primary aryl/heteroarylamine 2 in a suitable inert diluent such as water, dimethylsulfoxide (DMSO) and the like. The reaction employs an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, N-aryl/N-heteroaryl amino acid 3 is recovered by conventional methods including precipitation, chromatography, filtration and the like.

N-aryl/N-heteroaryl amino acid 3 is next esterified with alcohol 4 by conventional esterification conditions to provide for the esterified N-aryl/N-heteroaryl amino acid 5 which is a compound of formula I. For example, esterification procedures for $R^3$ groups containing an ester group can be achieved by using the methods of Losse, et al.[11] If desired, the esterification reaction can optionally be conducted on haloacetic acid 1 prior to amination with aryl/heteroarylamine 2.

In reaction (1), each of the reagents (haloacetic acid 1, primary aryl/heteroarylamine 2 and alcohol 3) are well known in the art with a plurality of each being commercially available.

In an alternative embodiment, the $R^1$ group can be coupled to an alanine ester (or other suitable amino acid ester) by conventional N-arylation. For example, a stoichiometric equivalent or slight excess of the amino acid ester can be dissolved in a suitable diluent such as DMSO and coupled with a haloaryl compound, X—$R^1$ where X is a halo group such as fluoro, chloro or bromo and $R^1$ is as defined above. The reaction is conducted in the presence of an excess of base such as sodium hydroxide to scavenge the acid generated by the reaction. The reaction typically proceeds at from 15° C. to about 250° C. and is complete in about 1 to 24 hours. Upon reaction completion, N-aryl amino acid ester is recovered by conventional methods including chromatography, filtration and the like.

In still another alternative embodiment, the esterified amino acids of formula I above can be prepared by reductive amination of a 2-oxocarboxylic acid ester (such as a pyruvate ester) ester in the manner illustrated in Reaction (2) below:

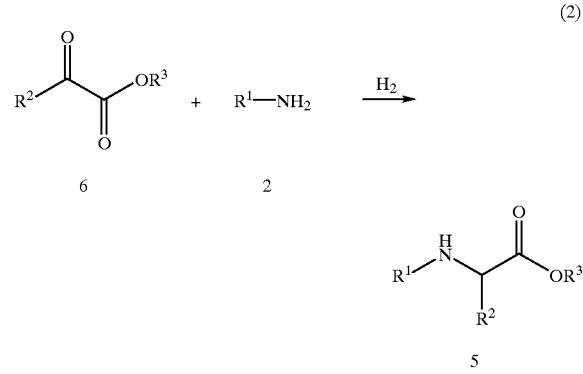

(2)

wherein $R^1$, $R^2$, $R^3$ are as defined above.

In reaction (2), approximately stoichiometric equivalents of pyruvate ester 6 and arylamine 2 are combined in an inert diluent such as methanol, ethanol and the like and the reaction solution treated under conditions which provide for imine formation (not shown). The imine formed is then reduced under conventional conditions by a suitable reducing agent such as sodium cyanoborohydride, $H_2$/palladium on carbon and the like to form the N-aryl amino acid ester 5. In a particularly preferred embodiment, the reducing agent is $H_2$/palladium on carbon which is incorporated into the initial reaction medium which permits imine reduction in situ in a one pot procedure to provide for the N-aryl amino acid ester 5.

The reaction is preferably conducted at from about 20° C. to about 80° C. at a pressure of from 1 to 10 atmospheres until reaction completion which typically occurs within 1 to about 24 hours. Upon reaction completion, N-aryl amino acid ester 5 is recovered by conventional methods including chromatography, filtration and the like.

A further embodiment for preparing the compounds of formula I above includes aromatic nucleophilic substitution of fluorobenzenes by the amine group of an amino acid as set forth in the Examples below.

In still a further embodiment, conventional transesterification techniques can be used to prepare a variety of different ester groups on the N-aryl amino acid esters 5. Numerous techniques are known in the art to effect transesterification and each technique merely replaces the —$OR^3$ group on the ester of the N-aryl amino acid ester 5 with a different —$OR^3$ group derived from the corresponding alcohol (i.e., $HOR^3$) and, in some cases, a catalyst such as titanium (IV) iso-propoxide is used to facilitate reaction completion. In one technique, the alcohol $HOR^3$ is first treated with sodium hydride in a suitable diluent such as toluene to form the corresponding $Na^+$ $OR^3$ which is then employed to effect transesterification with the N-aryl amino acid ester 5. The efficiency of this technique makes it particularly useful with high boiling and/or expensive alcohols.

In another transesterification technique, the N-aryl amino acid ester 5 to be transesterified is placed in a large excess of the alcohol which effects transesterification. A catalytic amount of sodium hydride is then added and the reaction proceeds quickly under conventional conditions to provide the desired transesterified product. Because this protocol requires the use of a large excess of alcohol, this procedure is particularly useful when the alcohol is inexpensive.

Transesterification provides a facile means to provide for a multiplicity of $R^3$ substituents on the compounds of formula I above. In all cases, the alcohols employed to effect transesterification are well known in the art with a significant number being commercially available.

Other methods for preparing the esters of this invention include, by way of example, first hydrolyzing the ester to the free acid followed by O-alkylation with a halo-$R^3$ group in the presence of a base such as potassium carbonate.

Still other methods for the preparation of esters are provided in the examples below.

Methods for the preparation of O-acyloxime esters include transesterification of the trichlorophenyl ester of a carboxylic acid with an oxime, and coupling of a carboxylic acid and an oxime using a carbodiimide coupling reagent. Similarly, methods for the preparation of pyrrole amides include conventional amidation techniques of the corresponding acid and pyrrole.

In these synthetic methods, the starting materials can contain a chiral center (e.g., alanine) and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of R,S enantiomers. Preferably, however, when a chiral product is desired, the chiral product corresponds to the L-amino acid derivative. Alternatively, chiral products can be obtained via purification techniques which separates enantiomers from a R,S mixture to provide for one or the other stereoisomer. Such techniques are well known in the art.

Pharmaceutical Formulations

When employed as pharmaceuticals, the compounds of formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 mL |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences,* Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 0.1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 0.1 to about 500 mg/kg/day.

As noted above, the compounds administered to a patient are in the form of pharmaceutical compositions described above. These compositions may be sterilized by conventional sterilization techniques, or may be sterile filtered. When aqueous solutions are employed, these may be packaged for use as is, or lyophilized, the lyophilized preparation being combined with a sterile aqueous carrier prior to administration. The pH of the compound preparations typically will be between 3 and 11, more preferably from 5–9 and most preferably from 7 and 8. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| BOC | = | tert-butoxycarbonyl |
| bd | = | broad doublet |
| bs | = | broad singlet |
| cc | = | cubic centimeter |
| d | = | doublet |
| dd | = | doublet of doublets |
| DMF | = | dimethylformamide |
| DMSO | = | dimethyl sulfoxide |
| EDC | = | 1-(3-dimethyaminopropyl)-ethylcarbodiimide hydrochloride |
| EDTA | = | ethylene diamine tetraacetic acid |
| eq. | = | equivalents |
| ether | = | diethyl ether |
| g | = | grams |
| hept. | = | heptuplet |
| m | = | multiplet |
| M | = | molar |
| max | = | maximum |
| mg | = | milligram |
| min. | = | minutes |
| mL | = | milliliter |
| mM | = | millimolar |
| mmol | = | millimole |
| N | = | normal |
| ng | = | nanogram |
| nm | = | nanometers |
| OD | = | optical density |
| pg | = | picogram |
| pM | = | picomolar |
| φ | = | phenyl |
| psi | = | pounds per square inch |
| q | = | quartet |
| quint. | = | quintuplet |
| rpm | = | rotations per minute |
| s | = | singlet |
| sept | = | septuplet |
| t | = | triplet |
| THF | = | tetrahydrofuran |
| tlc | = | thin layer chromatography |
| µL | = | microliter |
| UV | = | ultraviolet |
| w/v | = | weight to volume |

Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates the compound or reagent is commercially available from Fluka Chemical Corp., 980 South 2nd Street, Ronkonkoma, N.Y. 11779 USA; the term "Lancaster" indicates the compound or reagent is commercially available from Lancaster Synthesis, Inc., P.O. Box 100, Windham, N.H. 03087 USA; and the term "Sigma" indicates the compound or reagent is commercially available from Sigma, P.O. Box 14508, St. Louis, Mo. 63178 USA.

In the examples below, all temperatures are in degrees Celsius (unless otherwise indicated) and the following general procedures were used to prepare the compounds as indicated.

General Procedure A

Reductive Amination

To a solution of the arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi $H_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

General Procedure B

First Transesterification Technique

A solution of 1–5 equivalents of the desired alcohol was added to 1 equivalent of sodium hydride in toluene. After off-gassing had ceased, the compound to be transesterified, dissolved in toluene, was added. After 0.5 hours, the reaction was either heated to 40° C. and placed under house vacuum (~20 mmHg), or nitrogen was bubbled through the solution while it was heated at 90° C. The reaction was followed by tlc, and when the reaction was complete the solution was cooled and quenched with water or 1M HCl, and in smaller scale reactions diluted with ethyl acetate. The organic phase was extracted with saturated aqueous $NaHCO_3$, then washed with saturated aqueous NaCl and dried over $MgSO_4$. The solution was stripped free of solvent on a rotary evaporator, and the crude product residue was then further purified by chromatography. Alternatively, the reaction mixture was worked-up by evaporation of the solvents and direct chromatography of the crude mixture.

This procedure is particularly useful in the case of costly and/or high boiling alcohols.

General Procedure C

Second Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous $NaHCO_3$ was added. The organic phase was washed with saturated aqueous NaCl and dried over $MgSO_4$. The solution was stripped free of solvent on a rotary evaporator, and the crude product residue was then further purified by chromatography.

General Procedure D

Third Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous $NaHCO_3$ was added. The volume of the reaction mixture was reduced on a rotary evaporator until the excess alcohol was removed and then the remaining residue was taken up in ethyl acetate and additional water was added. The organic phase was washed with saturated aqueous NaCl and dried over $MgSO_4$. The solution was stripped free of solvent on a rotary evaporator, and the crude product residue was then further purified by chromatography.

This procedure is particularly employed in the case of low boiling, inexpensive alcohols, miscible with water.

General Procedure E

O-Alkylation Technique

To a carboxylic acid compound (prepared, for example, by reductive amination via General Procedure A to provide for the N-aryl amino acid ester, followed by hydrolysis via Procedure F) in DMF was added 1.5 equivalents $K_2CO_3$, followed by 1 equivalent of alkylating agent (e.g., tert-butyl bromoacetate). The reaction was stirred at room temperature for 2 hours, then was quenched with water and extracted into ethyl acetate. The organic phase was washed with saturated aqueous $NaHCO_3$, water, and saturated aqueous NaCl, and was then dried over $MgSO_4$. The solution was stripped free of solvent on a rotary evaporator to yield the crude product.

General Procedure F

Ester Hydrolysis to Free Acid

To a carboxylic ester compound (prepared, for example, by reductive amination via General Procedure A to provide for the N-aryl amino acid ester) in a 1:1 mixture of $CH_3OH/H_2O$ was added 2–5 equivalents of $K_2CO_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over $MgSO_4$. The solution was stripped free of solvent on a rotary evaporator to yield the crude product.

General Procedure G

N-Heteroarylation of Alanine

A solution of 1.1 equivalents of L-alanine and 2 equivalents NaOH in DMSO was stirred at room temperature for 1 hour, then 1 equivalent of 2-chlorobenzothiazole was added. The mixture was heated to 100° C. for 4 hours, then cooled to room temperature and poured onto ice. The pH of the resulting aqueous solution was adjusted to ~2, and the precipitated solid was removed by filtration. This solid was then dissolved in 1N NaOH and the resulting solution was filtered through a pad of Celite 545. The pH of the filtrate was adjusted to ~2, and the white precipitate was removed by filtration and washed with water to yield the crude product.

General Procedure H

EDC Coupling

To a 1:1 mixture of the desired acid and alcohol in $CH_2Cl_2$ at 0° C. was added 1.5 equivalents triethylamine, followed by 2.0 equivalents hydroxybenzotriazole monohydrate, then 1.25 equivalents of ethyl-3-(3-dimethylamino)-propyl carbodiimideHCl (EDC). The reaction was stirred overnight at room temperature, then transferred to a separatory funnel and washed with water, saturated aqueous $NaHCO_3$, 1N HCl, and saturated aqueous NaCl, and was then dried over $MgSO_4$. The solution was stripped free of solvent on a rotary evaporator to yield the crude product.

General Procedure I

Oxime or Amine Coupling Technique

The trichlorophenyl ester (1 eq) of a carboxylic acid was stirred in DMF or THF. The oxime or amine (1.2 eq) was added and the mixture was stirred at ambient temperature for 1–4 hours. In cases where the hydrochloride salt form of an amine was used, a suitable base such as N,N-diisopropylethylamine (1.2 eq) was also added. The resulting mixture was concentrated under reduced pressure to yield a crude product which was used without purification or was purified by silica gel chromatography and/or crystallization.

General Procedure J

Alkylation Technique

The amine (1 eq), the α-bromo ester (1.1 eq) and a suitable base (such as triethylamine) (2 eq) were stirred in chloroform. The resulting solution was heated at reflux for 4–12 hours. After cooling, the mixture was diluted with chloroform and washed with water. The organic portion was dried (sodium sulfate) and concentrated under reduced pressure. The crude product was purified by silica gel chromatography.

General Procedure K

Oxime or Alcohol Coupling Technique

The carboxylic acid (1 eq) was stirred in a suitable solvent (such as THF, dioxane or DMF). An alcohol or oxime (1–5 eq) was added. EDC S hydrochloride (1.2 eq) and hydroxybenzotriazole hydrate (1 eq) were added. A suitable base (such as 4-methylmorpholine or triethylamine) (0–1 eq) was added. A catalytic amount (0.1 eq) of 4-dimethylaminopyridine was added. The mixture was stirred at ambient temperature and under a dry atmosphere of nitrogen. After 20 hours, the mixture was concentrated under reduced pressure. The resulting concentrate was partitioned between ethyl acetate and water. The organic portion was separated and washed with aqueous sodium bicarbonate and brine. The organic portion was dried (sodium sulfate) and concentrated under reduced pressure. The crude product was used without purification or was purified by silica gel chromatography and/or crystallization.

General Procedure L

EDC Coupling

The carboxylic acid was dissolved in methylene chloride. The amino acid (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride (EDC) was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product. Pure products were obtained by flash chromatography in an appropriate solvent.

General Procedure M

Triflate Displacement

To a 0° C. solution of iso-butyl R-(+)-lactate in $CH_2Cl_2$ was added 1.1 equivalents of trifluoromethanesulfonic anhydride. After stirring at room temperature for 20 min, 1.1 equivalents of 2,6-lutidine was added and stiring was continued for 10 min. This solution was then transferred to a flask containing 1 equivalent the arylamine and 1 equivalent N,N-diisopropylethylamine in $CH_2Cl_2$ or $CH_3NO_2$ at 0° C. The reaction was held overnight at room temperature and then stripped free of solvent on a rotary evaporator. The residue was dissolved in ethyl acetate, washed with 5% citric acid, followed by saturated aqueous NaCl, dried over magnesium sulfate or sodium sulfate and then the solution was stripped free of solvent on a rotary evaporator to yield the crude product, which was then purified by chromatography.

General Procedure N

BOC Removal

The BOC-protected compound was added to a 1:1 mixture of $CH_2Cl_2$ and trifluoroacetic acid, and was stirred until tlc indicated complete conversion, typically 2 h. The solution was then stripped to dryness and the residue was taken up in ethyl acetate and extracted with dilute HCl. The acid reaction was neutralized and extracted with ethyl acetate. The organic phase was washed with saturated aqueous NaCl and dried over $MgSO_4$. The solution was stripped free of solvent on a rotary evaporator to yield the product.

General Procedure O

Synthesis of Pyruvate Esters

To a mixture of pyruvic acid (8.8 g, 0.1 mol) (Aldrich) in 100 mL of benzene was added isobutanol (14.82 g, 0.2 mol) and a catalytic amount of p-toluenesulfonic acid. The mixture was then refluxed using a Dean Stark apparatus. After 4 hours, the reaction appeared to be complete with the isolation of 1.8 g (0.1 mol) of water. The benzene and iso-butanol were removed on a rotary evaporator. The residue (14 g, 0.1 mol), which was primarily the pyruvate iso-butyl ester by nmr [$^1$H-Nmr ($CDCl_3$): δ=4.0 (d, 2H), 2.5 (s, 3H), 2.0 (m, 1H), 1.0 (d, 6H)], was used without further purification. By substituting other alcohols in place of isobutanol (e.g., ethanol, isopropanol, n-butanol, benzyl alcohol and the like), other esters of pyruvic acid can be prepared in a similar manner.

General Procedure P

Aromatic Nucleophilic Substitution of Fluorobenzenes

A mixture of 1.82 g (10 mmol) of D,L-alanine iso-butyl ester hydrochloride, the fluorobenzene (10 mmol) and 3 g of anhydrous potassium carbonate in 10 mL of DMSO was stirred at 120° C. for 2–5 hours. The reaction mixture was then cooled to room temperature and diluted with 100 mL of ethyl acetate. The ethyl acetate extract was washed with water (3x), dried over $MgSO_4$ and evaporated to dryness to afford the crude product, which was further purified by column chromatography.

General Procedure Q

Fourth Transesterification Technique

The ester to be transesterified was dissolved in a large excess of the alcohol and 0.3 equivalents of titanium(IV) isopropoxide (Aldrich) was added. The reaction was followed by tlc until complete and then the volatiles were removed at reduced pressure. The resulting crude material was then chromatographed to obtain the desired product.

General Procedure R

Synthesis on N-BOC Anilines

To a solution of the aniline in THF was added dropwise 1 equivalent of di-tert-butyl dicarbonate (Aldrich) in THF and then 1.5 equivalents of 10N aqueous sodium hydroxide at 0° C. After stirring at room temperature for 16 hours, or heating at 80° C. for 3 hours, if needed, the reaction mixture was diluted with ether and washed with $NaHCO_3$, brine, dried over sodium sulfate and potassium carbonate, concentrated at reduced pressure and chromatographed to afford the N-BOC aniline.

General Procedure S

Oxime Ester Formation

The trichlorophenyl ester (1 eq.) was stirred in DMF or THF. The oxime (1.2 eq.) was added and the mixture was stirred at ambient temperature for 1 to 4 hours. The resulting mixture was concentrated under reduced pressure and the residue was purified by silica gel chromatography and/or crystallization.

Example A

Synthesis of D,Lalanine iso-butyl ester hydrochloride

A mixture of 35.64 g (0.4 mol) of D,L-alanine (Aldrich), 44 mL (0.6 mol) of thionyl chloride (Aldrich) and 200 mL of iso-butanol was refluxed for 1.5 hours. The volatiles were removed at reduced pressure at 90° C. under reduced pressure to give the title compound as an oil, which was used without further purification.

NMR data was as follows:

$^1$H-nmr ($CDCl_3$): δ=8.72 (br s, 3H), 4.27 (q, J=7.4 Hz, 1H), 3.95 (m, 2H), 1.96 (s, 1H), 1.73 (d, J=7.2 Hz, 3H), 0.92 (d, J=6.7 Hz, 6H).

$^{13}$C-nmr ($CDCl_3$): δ=170.0, 72.2, 49.2, 27.5, 18.9, 16.1.

Example B

Synthesis of N-(3,4dichlorophenyl)alanine

Using the procedure set forth in U.S. Pat. No. 3,598,859, the disclosure of which is incorporated herein by reference in its entirety, N-(3,4-dichlorophenyl)alanine was prepared. Specifically, to a solution of 3,4-dichloroaniline (1 equivalent) (Aldrich) in isopropanol (about 500 mL per mole of 3,4-dichloroaniline) is added water (about 0.06 mL per mL of isopropanol) and 2-chloropropionic acid (2 equivalents) (Aldrich). This mixture is warmed to 40° C. and sodium bicarbonate (0.25 equivalents) is added in successive portions before heating under reflux for 4–5 days. After cooling, the reaction mixture is poured into water and the unreacted 3,4-dichloroaniline is removed by filtration. The filtrate is acidified to pH 3–4 with concentrated hydrochloric acid and the resultant precipitate is filtered, washed and dried to yield the title compound, m.p.=148–149° C.

Alternatively, following General Procedure F above and using N-(3,4-dichlorophenyl)alanine ethyl ester (from Example 1 below), the title compound was prepared.

Example C

Synthesis of N-(3,5-difluorophenyl)alanine

Using the procedure set forth in U.S. Pat. No. 3,598,859, N-(3,5-difluorophenyl)alanine was prepared using 3,5-difluoroaniline (Aldrich) and 2-chloropropionic acid (Aldrich).

Example D

Synthesis of Iso-butyl 2-bromopropionate

To a mixture of iso-butanol and 1.0 equivalent of pyridine in dry diethyl ether was added dropwise 1.3 equivalents of 2-bromopropionyl bromide at 0° C. After stirring at room temperature for 16 hours, the reaction was diluted with diethyl ether, washed with 1N HCl, water, aqueous NaHCO$_3$, brine and dried over magnesium sulfate or sodium sulfate. Removal of the solvents at reduced pressure gave the title compound as a clear oil.

Example E

Synthesis of N-(2-naphthyl)alanine 2,4,5-trichlorophenyl ester

N-(2-Naphthyl)alanine methyl ester (5.0 g, 20.6 mmol) (from Example 44 below) was dissolved in dioxane (100 mL). NaOH (30 mL, 1N) was added and the resulting solution was stirred for 1 hour. The reaction mixture was concentrated under reduced pressure. The resulting solid was dissolved in water and the aqueous mixture was washed with ether. The aqueous portion was adjusted to pH 3 with 1N HCl and extracted with ethyl acetate. The organic extracts were dried over magnesium sulfate or sodium sulfate and concentrated under reduced pressure to yield a white solid (4.35 g, 98%).

The resulting solid (4.35 g, 20 mmol) was dissolved in dichloromethane (300 mL). 2,4,5-Trichlorophenol (4.9 g, 25 mmol) (Aldrich) was added followed by dicyclohexylcarbodiimide (25 mL, 1M in dichloromethane) (Aldrich). After stirring for 18 hours, the mixture was filtered and concentrated to provide an oil which was purified by chromatography on silica gel using chloroform as the eluant (R$_f$=0.6). The title compound was obtained as a thick oil which slowly crystallized.

Example 1

Synthesis of N-(3,4-dichlorophenyl)alanine ethyl ester

Following General Procedure A above and using 3,4-dichloroaniline (Aldrich) and ethyl pyruvate (Aldrich), the title compound was prepared as an oil. The reaction was monitored by tlc on silica gel (R$_f$=0.4 in 25% EtOAc/hexanes) and purification was by preparative plate chromatography (silica gel using 25 % EtOAc/hexanes as the eluant).

NMR data was as follows:

$^1$H-nmr (CDCl$_3$): δ=7.2 (d, 1H); 6.7 (d, 1H,); 6.4 (dd, 1H); 4.30 (bs, 1H); 4.2 (q, 2H); 4.1 (q, 1H); 1.5 (d, 3H); 1.3 (t, 3H).

$^{13}$C-nmr (CDCl$_3$): δ=175; 146.7; 133; 131; 121; 114.9; 112.6; 72.0; 52.4; 28.3; 19.5.

C$_{11}$H$_{13}$Cl$_2$NO$_2$ (MW=262.14).

Example 2

Synthesis of N-(3-trifluoromethyl-4-chlorophenyl) alanine ethyl ester

Following General Procedure A above and using 4-chloro-3-(trifluoromethyl)aniline (Aldrich) and ethyl pyruvate (Aldrich), the title compound was prepared.

Analysis: Calc.: C, 48.74; H, 4.43; N, 4.74. Found: C, 48.48; H, 4.54; N, 4.94.

C$_{12}$H$_{13}$F$_3$ClNO$_2$ (MW=295.69); mass spectroscopy (MH$^+$) 295.

Example 3

Synthesis of N-(3,5-dichlorophenyl)alanine ethyl ester

Following General Procedure A above and using 3,5-dichloroaniline (Aldrich) and ethyl pyruvate (Aldrich), the title compound was prepared.

Analysis: Calc.: C, 50.40; H, 5.00; N, 5.34. Found: C, 50.50; H, 5.06; N, 5.25.

C$_{11}$H$_{13}$Cl$_2$NO$_2$ (MW=262.14); mass spectroscopy (MH$^+$) NA.

Example 4

Synthesis of N-(3,4-difluorophenyl)alanine ethyl ester

Following General Procedure A above and using 3,4-difluoroaniline (Aldrich) and ethyl pyruvate (Aldrich), the title compound was prepared. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.4 (m, 1H), 6.8 (d, 1H), 6.5 (m, 1H), 4.30 (bs, 1H), 4.2 (q, 2H), 4.1 (q, 1H), 1.5 (d, 3H), 1.3 (t, 3H).

$^{13}$C-nmr (CDCl$_3$): δ=175, 146.7, 135, 132, 125, 116, 113, 72, 52, 28, 19.

C$_{11}$H$_{13}$F$_2$NO$_2$ (MW=229.23); mass spectroscopy (MH$^+$) 230.

Example 5

Synthesis of N-(3,4-dichlorophenyl)alanine benzyl ester

Following General Procedure A above and using 3,4-dichloroaniline (Aldrich) and benzyl pyruvate (prepared by following General Procedure O above using benzyl alcohol in place of isobutanol), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 1H); 7.0 (m, 5H); 6.6 (d, 1H,); 6.4 (dd, 1H); 5.1 (s, 2H); 4.30 (bs, 1H); 4.08 (q, 1H); 1.94 (m, 1H); 1.47 (d, 3H); 0.91 (d, 6H).

$^{13}$C-nmr (CDCl$_3$): δ=174.5; 146.7; 133.5; 131.3; 121.3; 120.1; 114.9; 113.6; 72.0; 60.1; 52.4; 28.3; 19.5; 19.3.

C$_{16}$H$_{15}$Cl$_2$NO$_2$ (MW=324.31); mass spectroscopy (MH$^+$) 325.

Example 6

Synthesis of N-(3,4-dichlorophenyl)alanine iso-butyl ester

Following General Procedure A above and using 3,4-dichloroaniline (Aldrich) and iso-butyl pyruvate (prepared by following General Procedure O above), the title compound was prepared as an oil. The reaction was monitored by tlc on silica gel (Rf=0.55 in 25% EtOAc/hexanes) and purification was by preparative plate chromatography (silica gel using 25% EtOAc/hexanes as the eluant).

NMR data was as follows:

1H-nmr (CDCl$_3$): δ=7.18 (d, 1H, J=8.7 Hz), 6.66 (d, 1H, J=2.7 Hz), 6.43 (dd, 1H, J=8.7 Hz, J=2.7 Hz), 4.30 (s, 1H), 4.08 (q, 1H, J=6.9 Hz), 1.94 (sept, 1H, J=6.7 Hz), 1.47 (d, 3H, J=6.9 Hz), 0.91 (d, 6H, J=6.6 Hz).

$^{13}$C-nmr (CDCl$_3$) δ=174.5, 146.7, 133.5, 131.3, 121.3, 114.9, 113.6, 72.0, 52.4, 28.3, 19.5, 19.3.

C$_{13}$H$_{17}$Cl$_2$NO$_2$ (MW=290.19); mass spectroscopy (MH$^+$) 290.

Example 7

Synthesis of N-(3,4-dichlorophenyl)alanine iso-propyl ester

Following General Procedure A above and using 3,4-dichloroaniline (Aldrich) and isopropyl pyruvate (prepared by following General Procedure O above using isopropanol in place of iso-butanol), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 1H); 6.66 (d, 1H,); 6.43 (dd, 1H); 4.30 (bs, 1H); 4.08 (m, 1H); 1.94 (m, 1H); 1.47 (d, 3H); 0.91 (d, 6H).

$^{13}$C-nmr (CDCl$_3$): δ=174.5; 146.7; 133.5; 131.3; 121.3; 114.9; 113.6; 72.0; 52.4; 19.5.

C$_{12}$H15Cl$_2$NO$_2$ (MW=276.16); mass spectroscopy (MH$^+$) 277.

Example 8

Synthesis of N-(3,4-dichlorophenyl)alanine n-butyl ester

Following General Procedure A above and using 3,4-dichloroaniline (Aldrich) and n-butyl pyruvate (prepared by following General Procedure O above using n-butanol in place of iso-butanol), the title compound was prepared. The reaction was monitored by tlc on silica gel (Rf=0.7 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 1H); 6.66 (d, 1H,); 6.43 (dd, 1H); 4.30 (bs, 1H); 4.2 (m, 2H); 4.08 (q, 1H); 1.94 (m, 1H); 1.47 (m, 4H); 0.91 (t, 3H).

$^{13}$C-nmr (CDCl$_3$): δ=174.5; 146.7; 133.5; 131.3; 121.3; 114.9; 113.6; 72.0; 52.4; 28.3; 20.2; 19.5.

C$_{13}$H$_{17}$Cl$_2$NO$_2$ (MW=290.19); mass spectroscopy (MH$^+$) 291.

Example 9

Synthesis of N-(3,4-dichlorophenyl)alanine methyl ester (R,S isomers)

Following General Procedure A above and using 3,4-dichloroaniline (Aldrich) and methyl pyruvate (Aldrich), the title compound was prepared as an oil. The reaction was monitored by tlc on silica gel (Rf=0.55 in 25% EtOAc/hexanes) and purification was by flash chromatography (silica gel using 25% EtOAc/hexanes as the eluant).

NMR data was as follows:

$^1$H-nmr (CDCl$_3$): δ=7.19 (d, J=8.73 Hz, 1H), 6.66 (d, J=2.75 Hz, 1H), 6.43 (dd, J=8.73 Hz, 2.80 Hz, 1H), 4.25 (bd, J=8.25 Hz, 1H), 4.08 (m, 1H), 3.76 (s, 3H), 1.47 (d, J=6.90 Hz).

$^{13}$C-nmr (CDCl$_3$) δ=174.35, 145.96, 132.87, 130.70, 120.76, 114.38, 112.90, 52.43, 51.70, 18.67.

C$_{10}$H$_{11}$Cl$_2$NO$_2$ (MW=248.11); mass spectroscopy (MH$^+$) 247.

Example 10

Synthesis of N-(3,4dichlorophenyl)alanine cyclopentyl ester

Following transesterification General Procedure B above and using N-(3,4-dichlorophenyl)alanine methyl ester (from Example 9 above) and cyclopentanol (Aldrich), the title compound was prepared as an oil. The reaction was monitored by silica gel tlc (Rf=0.66 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.19 (d, 1H, J=8.7 Hz), 6.66 (d, 1H, J=2.7 Hz), 6.43 (dd, 1H, J=8.7 Hz, J=2.7 Hz), 5.22 (m, 1H), 4.27 (d, 1H, J=8.1 Hz), 4.02 (quint, 1H, J=7.5 Hz), 1.74 (m, 8H), 1.43 (d, 3H, J=6.9 Hz).

$^{13}$C-nmr (CDCl$_3$): δ=174.3, 146.7, 133.4, 131.2, 121.2, 114.9, 113.7, 78.9, 52.5, 33.2, 24.2, 24.1, 19.1.

C$_{14}$H$_{17}$Cl$_2$NO$_2$ (MW=302.20); mass spectroscopy (MH$^+$) 301.

Example 11

Synthesis of N-(3,4-dichlorophenyl)alanine n-propyl ester

Following General Procedure A above and using 3,4-dichloroaniline (Aldrich) and n-propyl pyruvate (prepared by following General Procedure O above using n-propanol in place of iso-butanol), the title compound was prepared as an oil. The reaction was monitored by tlc on silica gel (Rf=0.5 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.30 (bs, 1H); 4.2 (q, 2H); 4.08 (q, 1H); 1.94 (m, 2H); 1.5 (d, 3H); 0.95 (t, 3H).

$^{13}$C-nmr (CDCl$_3$): δ=178; 144.7; 130.2; 120.62; 115.11; 71.82; 52.90.

C$_{12}$H$_{15}$Cl$_2$NO$_2$ (MW=276.16); mass spectroscopy (MH$^+$) 277.

Example 12

Synthesis of N-(3,4-dichlorophenyl)alanine allyl ester

Following transesterification General Procedure B above and using N-(3,4-dichlorophenyl)alanine methyl ester (from Example 9 above) and allyl alcohol (Aldrich), the title compound was prepared as an oil. The reaction was monitored by silica gel tlc (Rf=0.62 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.19 (d, 1H, J=8.7 Hz), 6.67 (d, 1H, J=2.8 Hz), 6.44 (dd, 1H, J=8.7 Hz, J=2.8 Hz), 5.90 (m, 1H), 5.30 (m, 2H), 4.64 (m, 2H), 4.26 (m, 1H, 4.10 (m, 1H), 1.48 (d, 3H, J=6.9 Hz).

$^{13}$C-nmr (CDCl$_3$): δ=174.1, 146.6, 133.5, 132.1, 131.3, 121.4, 119.6, 115.0, 113.6, 66.5, 52.4, 19.3.

C$_{12}$H$_{13}$Cl$_2$NO$_2$ (MW=274.15); mass spectroscopy (MH$^+$) 273.

Example 13

Synthesis of N-(3,4-dichlorophenyl)alanine 4-methylpentyl ester

Following transesterification General Procedure B above and using N-(3,4-dichlorophenyl)alanine methyl ester (from Example 9 above) and 4-methylpentanol (Aldrich), the title compound was prepared as an oil. The reaction was monitored by silica gel tlc (Rf=0.70 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.18 (d, 1H, δ=8.7 Hz), 6.66 (d, 1H, J=2.7 Hz), 6.43 (dd, 1H, J=8.7 Hz, J=2.7 Hz), 4.28 (m, 1H), 4.10 (m, 3H), 1.55 (m, 6H), 1.19 (m, 2H), 0.87 (d, 3H, J=6.6 Hz).

$^{13}$C-nmr (CDCl$_3$): δ=174.6, 146.7, 133.4, 131.3, 121.3, 115.0, 113.6, 66.4, 52.4, 35.4, 28.2, 27.0, 23.0, 19.3.

C$_{15}$H$_{21}$Cl$_2$NO$_2$ (MW=318.25); mass spectroscopy (MH$^+$) 317.

Example 14

Synthesis of N-(3,4-dichlorophenyl)alanine 2,2-dimethyl-1,3-dioxolane-4-methyl ester Following transesterification General Procedure B above and using N-(3,4-dichlorophenyl)alanine methyl ester (from Example 9 above) and 2,2-dimethyl-1,3-dioxolane-4-methanol (solketal) (Aldrich), the title compound was prepared as a mixture of diastereomers. The reaction was monitored by silica gel tdc (Rf=0.32 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.19 (d, 1H, J=8.7 Hz), 6.66 (d, 1H, 2.7 Hz), 6.43 (dd, 1H, J=8.7 Hz, J=2.7 Hz), 4.22 (m, 6H), 3.70 (m, 1H), 1.43 (m, 9H).

$^{13}$C-nmr (CDCl$_3$): δ=174.34, 174.32, 146.5, 133.5, 131.3, 121.5, 115.0, 113.6, 110.52, 110.51, 73.97, 73.89, 66.6, 66.01, 65.95, 52.42, 52.37, 27.3, 25.8, 19.3.

C$_{15}$H$_{19}$Cl$_2$NO$_4$ (MW=348.23); mass spectroscopy (MH$^+$) 347.

Example 15

Synthesis of N-(3,4-dichlorophenyl)alanine cyclohexylmethyl ester

Following transesterification General Procedure B above and using N-(3,4-dichlorophenyl)alanine methyl ester (from Example 9 above) and cyclohexylmethanol (Aldrich), the title compound was prepared.

NMR data was as follows:

$^1$H-nmr (CDCl$_3$): δ=7.19 (d, 1H), 6.68 (d, 1H), 6.45 (dd, 1H), 4.26 (bd, 1H), 4.10 (m, 1H), 3.95 (d, 2H), 1.70–1.55 (m, 6H), 1.50 (d, 3H), 1.35–0.85 (m, 5H).

$^{13}$C-nmr (CDCl$_3$): δ=174.58, 146.72, 133.48, 131.27, 121.34, 114.98, 113.72, 71.06, 52.52, 37.68, 30.10, 26.83, 26.17, 19.32.

C$_{15}$H$_{21}$Cl$_2$NO$_2$ (MW=318.25); mass spectroscopy (MH$^+$) 317.

Example 16

Synthesis of N-(3,4-dichlorophenyl)alanine tert-butyloxycarbonylmethyl ester

Following General Procedure E above and using N-(3,4-dichlorophenyl)alanine (from Example B above) and tert-butyl bromoacetate (Aldrich), the title compound was prepared as a solid. The reaction was monitored by silica gel tlc (Rf=0.57 in 25% EtOAc/hexanes). Purification was by recrystallization from ethanol.

NMR data was as follows:

$^1$H-nmr (CDCl$_3$): δ=7.19 (d, 1H), 6.68 (d, 1H), 6.45 (dd, 1H), 4.55 (m, 2H), 4.20 (m, 2H), 1.55 (d, 3H), 1.45 (s, 9H).

$^{13}$C-nmr (CDCl$_3$): δ=173.9, 166.9, 146.5, 133.5, 131.3, 115.1, 113.6, 83.4, 62.2, 52.2, 28.6, 19.3.

C$_{15}$H$_{19}$Cl$_2$NO$_4$ (MW=348.23); mass spectroscopy (MH$^+$) 347.

Example 17

Synthesis of N-(3,4-dichlorophenyl)leucine iso-butyl ester

Following General Procedure A above and using 3,4-dichloroaniline (Aldrich) and iso-butyl 4-methyl-2-oxopentanoate (prepared by following General Procedure O above using 4-methyl-2-oxovaleric acid (Fluka) and iso-butanol), the title compound was prepared as an oil. The reaction was monitored by tlc on silica gel (Rf=0.6 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.5 (d, 1H); 6.4 (dd, 1H); 4.30 (bs, 1H); 4.08 (q, 1H); 3.8(m, 2H); 1.8 (m, 3H); 0.91 (m, 12H).

$^{13}$C-nmr (CDCl$_3$): δ=174.5; 146.7; 133.5; 131.3; 121.3; 114.9; 113.6; 72.0; 52; 28.3; 20.1; 19.5.

C$_{16}$H$_{23}$Cl$_2$NO$_2$ (MW=332.27); mass spectroscopy (MH$^+$) 333.

Example 18

Synthesis of 2-[N-(3,4-dichlorophenyl)amino] pentanoic acid iso-butyl ester

Following General Procedure A above and using 3,4-dichloroaniline (Aldrich) and iso-butyl 2-oxopentanoate (prepared by following General Procedure O above using 2-oxovaleric acid (Fluka) and iso-butanol), the title compound was prepared as an oil. The reaction was monitored by tlc on silica gel (Rf=0.5 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.3 (d, 1H); 3.8 (m, 3H); 1.9 (m, 6H); 1.0 (t, 3H), 0.9 (m, 6H).

$^{13}$C-nmr (CDCl$_3$): δ=178; 144.7; 130.2; 120.62; 115.11; 71.82; 52.90; 28.30; 19.53.

C$_{15}$H$_{21}$Cl$_2$NO$_2$ (MW=318.3); mass spectroscopy (MH$^+$) 319.

Example 19

Synthesis of N-(4-cyanophenyl)alanine iso-butyl ester

Following General Procedure P above and using 4-fluorobenzonitrile (Aldrich) and D,L-alanine iso-butyl ester hydrochloride (from Example A above), the title compound was prepared as an oil. The product was recovered by column chromatography on silica gel using 1:5 EtOAc/hexanes as the eluant.

NMR data was as follows:

$^1$H-nmr (CDCl$_3$): δ=7.44 (d, J=8.8 Hz, 2H), 6.57 (d, J=8.8 Hz, 2H), 4.74 (d, J=8.1 Hz, 1H), 4.18 (t, J=7.4 Hz, 1H), 3.95 (m, 2H), 1.94 (m, 1H), 1.51 (d, δ=6.9 Hz, 3H), 0.91 (d, J=6.7 Hz, 6H).

$^{13}$C-nmr (CDCl$_3$): δ=173.4, 149.7, 133.8, 120.1, 112.7, 99.8, 71.6, 51.2, 27.7, 18.9, 18.6.

C$_{14}$H$_{18}$N$_2$O$_2$ MW=246.31; mass spectroscopy (MH$^+$) 247.

Example 20

Synthesis of N-(3-chloro-4-cyanophenyl)alanine iso-butyl ester

Following General Procedure P above and using 2-chloro-4-fluorobenzonitrile (Aldrich) and D,L-alanine iso-butyl ester hydrochloride (from Example A above), the title compound was prepared. The product was recovered by column chromatography on silica gel using 1:5 EtOAc/hexanes as the eluant.

NMR data was as follows:

$^1$H-nmr (CDCl$_3$): δ=7.40 (d, J=8.5 Hz, 1H), 6.62 (d, J=2.3 Hz, 1H), 6.48 (dd, J=2.4, 8.6 Hz, 1H), 4.90 (d, J=7.6 Hz, 1H), 4.16 (quintet, J=7.1 Hz, 1H), 3.96 (dd, J=2.2, 6.7 Hz, 2H), 1.97 (m, 1H), 1.51 (d, J=7.0 Hz, 3H), 0.93 (d, J=6.7 Hz, 6H).

$^{13}$C-nmr (CDCl$_3$): δ=173.0, 150.4, 138.3, 134.9, 117.3, 112.8, 111.3, 100.6, 71.7, 51.1, 27.7, 18.9, 18.4.

C$_{14}$H$_{17}$N$_2$O$_2$Cl MW=280.76; mass spectroscopy (MH$^+$) 281.

Example 21

Synthesis of N-(3,4-dichloro)alanine iso-butyl ester (S isomer)

Following General Procedure M above and using 3,4-dichloroaniline (Aldrich) and iso-butyl R-(+)-lactate (Aldrich), the title compound was prepared as an oil. The reaction was monitored by silica gel tlc (Rf=0.55 in 25% EtOAc/hexanes). Purification was column chromatography.

NMR data was as follows:

$^1$H-nmr (CDCl$_3$): δ=7.19 (d, J=8.73, 1H), 6.67 (d, J=2.75, 1H), 6.45 (dd, J=8.73, J=2.75, 1H), 4.28 (bd, J=8.36, 1H), 4.09 (quint, 1H), 3.94 (d, J=6.66, 2H), 1.95 (hept, J=6.71, 1H), 1.49 (d, J=6.90, 3H), 0.92 (d, J=6.04, 6H).

$^{13}$C-nmr (CDCl$_3$): δ=174.57, 146.67, 133.47, 131.28, 121.29, 114.93, 113.63, 71.01, 52.43, 28.30, 19.55, 19.33.

C$_{13}$H$_{17}$Cl$_2$NO$_2$ (MW=290.19); mass spectroscopy (MH$^+$) 290.

Example 22

Synthesis of N-(3,4-dichloro)alanine tetrahydrofuran-3-yl-methyl ester

Following transesterification General Procedure B above and using N-(3,4-dichlorophenyl)alanine methyl ester (from Example 9 above) and tetrahydro-3-furanmethanol (Aldrich), the title compound was prepared as an oil. The reaction was monitored by silica gel tlc (Rf=0.33 in 25% EtOAc/hexanes). Purification was by preparative plate chromatography (silica gel using 25% EtOAc/hexanes as the eluant).

NMR data was as follows:

$^1$H-nmr (CDCl$_3$): δ7.18 (d, 1H, J=8.7 Hz), 6.65 (d, 1H, J=2.7 Hz), 6.42 (dd, 1H, J=8.7 Hz, J=2.7 Hz), 4.30 (m, 1H), 4.09 (m, 3H), 3.78 (m, 3H), 3.53 (m, 1H), 2.56 (m, 1H), 1.94 (m, 1H), 1.58 (m, 1H), 1.46 (d, 3H, J=6.9 Hz).

$^{13}$C-nmr (CDCl$_3$): δ=174.5, 146.6, 133.5, 131.3, 121.4, 114.9, 113.6, 70.86, 70.83, 68.2, 67.31, 67.29, 52.4, 38.7, 29.36, 29.33, 19.2.

C$_{14}$H$_{17}$Cl$_2$NO$_3$ (MW=318.20); mass spectroscopy (MH$^+$) 318.

Example 23

Synthesis of N-(3,5-dichlorophenyl)alanine n-propyl ester

Following General Procedure A above and using 3,5-dichloroaniline (Aldrich) and n-propyl pyruvate (which can be prepared by following General Procedure O above using n-propanol in place of iso-butanol), the title compound could be prepared.

Example 24

Synthesis of 2-[N-(3,4-dichlorophenyl)amino] butanoic acid iso-butyl ester

Following General Procedure A above and using 3,4-dichloroaniline (Aldrich) and iso-butyl 2-oxobutanoate (prepared by following General Procedure O above using 2-oxobutyric acid (Aldrich) and iso-butanol), the title compound was prepared as an oil. The reaction was monitored by tlc on silica gel (Rf=0.3 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.3 (d, 1H); 3.8 (m, 3H); 1.9 (m, 3H); 1.0 (t, 3H); 0.9(m, 6H).

$^{13}$C-nmr (CDCl$_3$): δ=178; 144.7; 130.2; 120.62; 115.11; 71.82; 52.90; 28.30; 20.5; 19.53.

C$_{14}$H$_{19}$Cl$_2$NO$_2$ (MW=304.22); mass spectroscopy (MH$^+$) 305.

Example 25

Synthesis of N-(4-chlorophenyl)alanine iso-butyl ester

Following General Procedure A above and using 4-chloroaniline (Aldrich) and iso-butyl pyruvate (prepared by following General Procedure O above), the title compound was prepared as an oil. The reaction was monitored by tlc on silica gel (Rf=0.6 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 2H), 6.66 (d, 2H), 4.30 (bs, 1H), 4.08 (q, 1H), 1.94 (sept, 1H), 1.47 (d, 3H), 0.91 (d, 6H).

$^{13}$C-nmr (CDCl$_3$): δ=174.5, 146.7, 133.5, 131.3, 121.3, 114.9, 113.6, 72.0, 52.4, 28.3, 19.5, 19.3.

C$_{13}$H$_{18}$ClNO$_2$ (MW=255.75); mass spectroscopy (MH$^+$) 256.

Example 26

Synthesis of N-(3,5-dichlorophenyl)alanine isobutyl ester

Following General Procedure A above and using 3,5-dichloroaniline (Aldrich) and iso-butyl pyruvate (prepared by following General Procedure O above), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 2H), 6.66 (m, 1H), 4.30 (bs, 1H), 4.08 (q, 1H), 1.94 (m, 1H), 1.47 (d, 3H), 0.91 (d, 6H).

$^{13}$C-nmr (CDCl$_3$): δ=175; 146.7; 133; 131; 121; 114.9; 112.6; 72.0; 52.4; 28.3; 19.5.

C$_{13}$H$_{17}$Cl$_2$NO$_2$ (MW=290.2); mass spectroscopy (MH$^+$) 291.

Example 27

Synthesis of N-(4-ethylphenyl)alanine methyl ester

A solution of 0.68 g (5 mmol) of 4'-aminoacetophenone (Aldrich), 0.60 mL of 90% methyl pyruvate (Aldrich) and 0.05 g (0.25 mmol) of p-toluenesulfonic acid in ethanol was hydrogenated in the presence of a catalytic amount of 10% Pd/C at from 30 to 15 psi of hydrogen for 16 hours. The catalyst was removed by filtering the reaction mixture through Celite and the solvent was evaporated to provide the crude product. The product was purified by column chromatography (silica gel using 1:9 EtOAc/hexanes as the eluant) to provide the title compound.

NMR data was as follows:

$^1$H-nmr (CDCl$_3$): δ=1.19 (t, J=7.6 Hz, 3H), 1.47 (d, J=6.8 Hz, 3H), 2.54 (q, J=7.6 Hz, 2H), 3.74 (s, 3H), 4.04 (bs, 1H), 4.13 (m, 1H), 6.57 (d, J=8.5 Hz, 2H), 7.03 (d, J=8.4 Hz, 2H).

$^{13}$C-nmr (CDCl$_3$): δ=15.8, 18.0, 27.9, 52.17, 52.19, 113.5, 128.6, 134.1, 144.4, 175.3.

C$_{12}$H$_{17}$NO$_2$ MW=207.27; mass spectroscopy (MH$^+$) 208.

Example 28

Synthesis of N-(4-(1-ethoxy)ethylphenyl)alanine methyl ester

Following the procedure for Example 27 above, the title compound was isolated as another reaction product by column chromatography (silica gel using 1:9 EtOAc/hexanes as the eluant).

NMR data was as follows:

$^1$H-nmr (CDCl$_3$): δ=1.15 (t, J=7.0 Hz, 3H), 1.40 (d, J=6.5 Hz, 3H), 1.47 (d, J=6.1 Hz, 3H), 3.31 (q, J=5.1 Hz, 2H), 3.74 (s, 3H), 4.14 (m, 2H), 4.29 (q, J=6.4 Hz, 1H), 6.57 (d, J=8.5 Hz, 2H), 7.12 (d, J=8.4 Hz, 2H).

$^{13}$C-nmr (CDCl$_3$): δ=15.4, 19.0, 23.9, 51.9, 52.2, 63.4, 77.3, 113.1, 127.3, 133.6, 145.8, 175.1.

C$_{14}$H$_{21}$NO$_3$ MW=251.33; mass spectroscopy (MH$^+$) 251.

Example 29

Synthesis of N-(3,4-dichloro)alanine 2,2-dimethylpropyl ester (R,S isomers)

Following transesterification General Procedure Q above and using N-(3,4-dichlorophenyl)alanine methyl ester (from Example 9 above) and neopentyl alcohol (Aldrich), the title compound was prepared. The reaction was monitored by silica gel tlc (Rf=0.72 in 25% EtOAc/hexanes). Purification was by flash chromatography (silica gel using 25% EtOAc/hexanes as the eluant).

NMR data was as follows:

$^1$H-nmr (CDCl$_3$): δ=7.19 (d, 1H, J=8.7 Hz), 6.68 (d, 1H, J=2.7 Hz), 6.45 (dd, 1H, J=8.7 Hz, J=2.7 Hz), 4.29 (m, 1H), 4.11 (m, 1H), 3.85 (m, 2H), 1.49 (d, 3H, J=6.9 Hz), 0.93 (s, 9H).

$^{13}$C-nmr (CDCl$_3$): δ=174.6, 146.7, 133.5, 131.3, 121.3, 114.9, 113.7, 75.2, 52.4, 32.0, 26.9, 19.4.

C$_{14}$H$_{19}$Cl$_2$NO$_2$ (MW=304.22); mass spectroscopy (MH$^+$) 303.

Example 30

Synthesis of N-(3,4-dichlorophenyl)glycine iso-butyl ester 3,4-Dichloroaniline (Aldrich) was treated with di-tert-butyl dicarbonate (Aldrich) using conventional procedures to produce the N-BOC aniline. The N-BOC aniline was treated with sodium hydride in THF and then with isobutyl 2-bromoacetate (from Example D above) to produce the N-BOC N-(3,4-dichlorophenyl)glycine iso-butyl ester. The BOC group was then removed using General Procedure N above to afford the title compound. The reaction was monitored by tlc on silica gel (Rf=0.78 in 50% EtOAc/hexanes) and purification was by preparative plate chromatography (silica gel using 50% EtOAc/hexanes as the eluant).

NMR data was as follows:

$^1$H-nmr (CDCl$_3$): δ=7.19 (dd, J=4.1, 4.7, 3.4, 1H); 6.65 (d, J=2.7, 1H); 6.44 (dd, J=2.7, 4.5, 4.2, 1H): 4.4 (m, 1H): 3.97 (dd, J=3.6, 3.0, 2.3, 2H); 3.87 (s, 2H); 1.9 (m, 1H); 0.93 (d, J=6.7, 6H).

$^{13}$C-nmr (CDCl$_3$): δ=171.2, 147.0, 133.5, 131.3, 121.2, 114.5, 113.3, 72.2, 46.0, 28.2, 19.6.

C$_{12}$H$_{15}$Cl$_2$NO$_2$ (MW=276); mass spectroscopy (MH$^+$) 277.

Example 31

Synthesis of N-(3,4-dichlorophenyl)alanine 2-ethylbutyl ester

Following General Procedure A above and using 3,4-dichloroaniline (Aldrich) and 2-ethylbutyl pyruvate (prepared by following General Procedure O above using 2-ethylbutanol (Aldrich) in place of iso-butanol), the title compound was prepared as an oil. The reaction was monitored by tlc on silica gel (Rf=0.6 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.2 (t, 2H); 4.1 (q, 1H); 1.5 (d, 3H); 1.4 (m, 4H); 1.0 (m, 6H).

$^{13}$C-nmr (CDCl$_3$): δ=178; 144.7; 130.2; 120.62; 115.11; 70.7; 51.90; 26.3; 19.53, 18.5.

C$_{15}$H$_{21}$Cl$_2$NO$_2$ (MW=318.25); mass spectroscopy (MH$^+$) 319.

Example 32

Synthesis of N-(3-chloro-4-iodophenyl)alanine iso-butyl ester

Following General Procedure R above and using 3-chloro-4-iodoaniline (Aldrich), N-BOC-3-chloro-4-iodoaniline was prepared. To a stirred slurry of 5.0 equivalents of sodium hydride in DMF was added 1.0 equivalent of N-BOC-3-chloro-4-iodoaniline and then 1.1 equivalents of iso-butyl 2-bromopropionate (from Example D above) were slowly added. The reaction was heated to 100° C. for 10 hours, cooled, diluted with dichloromethane and washed with cold 1N HCl, water and brine. The solvents were removed at reduced pressure and the residue was chromatographed to provide N-BOC-N-(3-chloro-4-iodophenyl)alanine iso-butyl ester as a clear oil. Following General Procedure N above, the BOC group was removed from N-BOC-N-(3-chloro-4-iodophenyl)alanine iso-butyl ester to provide the title compound. The BOC-removal reaction was monitored by tlc on silica gel (Rf=0.58 in 30% EtOAc/hexanes) and purification was by preparative plate chromatography (silica gel using 30% EtOAc/hexanes as the eluant). The compound was further purified by chromatography on an HPLC chiral column (Chiralcel OD).

NMR data was as follows:

$^1$H-nmr (CDCl$_3$): δ=7.52 (d, J=8.7, 1H); 6.72 (d, J=2.7, 1H); 6.25 (dd, J=2.7, 5.9, 2.7, 1H); 4.35 (d, J=6.6, 1H): 4.08 (quintex, J=7.2, 6.7, 1H); 3.93 (d, J=6.7, 2H): 1.94 (m, 1H); 1.47 (d, J=6.9, 3H); 0.92 (d, J=6.9, 6H).

$^{13}$C-nmr (CDCl$_3$): δ=174.5, 148.3, 140.7, 139.5, 114.4, 114.3, 82.6, 72.0, 52.2, 28.3, 19.6, 19.3.

$C_{13}H_{17}ClINO_2$ (MW=381.5); mass spectroscopy (MH$^+$) 382.

Example 33

Synthesis of N-(4-azidophenyl)alanine iso-butyl ester

Following General Procedure A above and using 4-azidoaniline (Aldrich) and iso-butyl pyruvate (prepared by following General Procedure O above), the title compound was prepared as an oil. The reaction was monitored by tlc on silica gel (Rf=0.3 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.3 (d, 2H), 6.8 (d, 2H), 4.30 (bs, 1H), 4.08 (q, 1H), 1.94 (sept, 1H), 1.47 (d, 3H), 0.91 (d, 6H).

$^{13}$C-nmr (CDCl$_3$): δ=174.5, 148.7, 131.5, 130.3, 121.3, 114.9, 113.6, 72.0, 52.4, 28.3, 19.5, 19.3.

$C_{13}H_{18}N_4O_2$ (MW=262.31); mass spectroscopy (MH$^+$) 263.

Example 34

Synthesis of N-[(4-phenylcarbonyl)phenyl]alanine iso-butyl ester

Following General Procedure A above and using 4'-aminobenzophenone (Aldrich) and iso-butyl pyruvate (prepared by following General Procedure O above), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.7 (d, 2H), 7.1 (m, 5H), 6.9 (d, 2H), 4.30 (bs, 1H), 4.08 (q, 1H), 1.94 (sept, 1H), 1.47 (d, 3H), 0.91 (d, 6H).

$^{13}$C-nmr (CDCl$_3$): δ=199, 178.5, 149.7, 131.5, 130.3, 126, 121.3, 114.9, 113.6, 72.0, 52.4, 28.3, 19.5, 19.3.

$C_{20}H_{23}NO_3$ (MW=325.41); mass spectroscopy (MH$^+$) 326.

Example 35

Synthesis of N-(3,5-difluorophenyl)alanine iso-butyl ester

Following General Procedure H above and using N-(3,5-difluorophenyl)alanine (from Example C above) and isobutanol, the title compound was prepared as an oil. The reaction was monitored by tlc on silica gel (Rf=0.9 in 3% methanol/methylene chloride) and purification was by preparative plate chromatography (silica gel using 3% methanol/methylene chloride as the eluant).

NMR data was as follows:

$^1$H-nmr (CDCl$_3$): δ=6.1 (m, 3H), 4.5 (bs, 1H), 4.1 (d, 1H), 3.95 (m, 2H), 2.0 (m, 1H), 1.5 (d, J=7 Hz, 3H), 0.95(d, J=6 Hz, 6H).

$^{13}$C-nmr (CDCl$_3$): δ=174.44, 166.40, 166.19, 163.16, 162.95, 149.43, 96.73, 96.60, 96.48, 96.35, 94.06, 93.72, 93.37, 72.03, 52.30, 28.29, 19.47, 19.23.

$C_{13}H_{17}F_2NO_2$ (MW=290.2); mass spectroscopy (MH$^+$) 291.

Example 36

Synthesis of N-(3,4-dichlorophenyl)alanine O-acylacetamidoxime ester

Following General Procedure K above and using N-(3,4-dichlorophenyl)alanine (from Example B above) and acetamide oxime (prepared according to the procedures described in *J. Org. Chem.*, 46, 3953 (1981)), the title compound was prepared as a semisolid. The reaction was monitored by tlc on silica gel (Rf=0.4 in ethyl acetate) and purification was by preparative plate chromatography (silica gel using ethyl acetate as the eluant).

NMR data was as follows:

$^1$H-nmr (DMSO-d$_6$): δ=7.27 (d, 1H), 6.81 (s, 1H) 6.4 (broad s, 2H), 6.62 (d, 1H), 6.45 (d, 1H), 4.22 (m, 1H), 1.74 (s, 3H), 1.40 (d, 3H).

$C_{11}H_{13}Cl_2N_3O_2$ (MW=290.15); mass spectroscopy (MH$^+$) 291.

Example 37

Synthesis of N-(3,4-dichlorophenyl)alanine pyrrolyl amide

Following General Procedure L above and using N-(3,4-dichlorophenyl)alanine (from Example B above) and pyrrole (Aldrich), the title compound was prepared as an oil. The reaction was monitored by tlc on silica gel (Rf=0.28 in 10% ethyl acetate/hexanes) and purification was by preparative plate chromatography (silica gel using 10% ethyl acetate/hexanes as the eluant).

NMR data was as follows:

$^1$H-nmr (CDCl$_3$): δ=7.36 (d, J=2.2, 2H); 7.20 (d, J=8.7, 1H); 6.71 (d, J=2.7, 1H); 6.5 (m, 1H); 6.38 (t, J=2.4, 2H); 4.8 (m, 1H); 4.57 (d, J=8.7, 1H); 1.59 (d, J=6.8, 3H).

$^{13}$C-nmr (CDCl$_3$): δ=171.9, 146.1, 133.6, 131.5, 121.9, 119.6, 115.4, 114.7, 113.8, 51.8, 20.2.

$C_{13}H_{12}Cl_2N_2O$ (MW=283); mass spectroscopy (MH$^+$) 284.

Example 38

Synthesis of N-(3,4-dichlorophenyl)alanine O-acylbutyramideoxime ester

Following General Procedure I above and using N-(3,4-dichlorophenyl)alanine 2,4,6-trichlorophenyl ester (prepared from N-(3,4-dichlorophenyl)alanine methyl ester (from Example 9) using essentially the same procedure as described in Example E above) and butyramide oxime (prepared according to the procedures described in *J. Org. Chem.*, 46, 3953 (1981)), the title compound was prepared as a semisolid. The reaction was monitored by tlc on silica gel (Rf=0.25 in 50% ethyl acetate/hexanes) and purification was by preparative plate chromatography (silica gel using 50% ethyl acetate/hexanes as the eluant).

NMR data was as follows:

$^1$H-nmr (d$_6$-DMSO): δ=7.27 (d, 1H), 6.83 (s, 1H) 6.38 (broad s, 2H), 6.61 (d, 1H), 6.46 (d, 1H), 4.25 (m, 1H), 2.02 (t, 2H), 1.55 (m, 2H), 1.40 (d, 3H), 0.88 (t, 3H).

$C_{13}H_{17}Cl_2N_3O_2$ (MW=318.20); mass spectroscopy (MH$^+$) 319.

Example 39

Synthesis of 2-[N-(naphth-2-yl)amino]butanoic acid ethyl ester

Following General Procedure J above and using 2-aminonaphthalene (Aldrich) and ethyl 2-bromobutyrate (Aldrich), the title compound was prepared as a solid, m.p. 81–83° C. The reaction was monitored by silica gel tlc (Rf=0.5 in CHCl$_3$). Purification was by chromatography (silica gel using chloroform as the eluant).

NMR data was as follows: $^1$H-nmr (d$^6$-DMSO): δ=7.63 (m, 2H), 7.54 (d, 1H), 7.31(t, 1H), 7.12 (t, 1H), 7.03 (d, 1H), 6.62 (s, 1H), 6.32 (d, 1H), 4.15 (m, 3H), 1.42 (d, 3H), 1.19 (t, 3H).

$C_{16}H_{19}NO_2$ (MW=257.34); mass spectroscopy (MH$^+$) 258.

Example 40

Synthesis of N-(2-naphthyl)alanine iso-butyl ester

Following General Procedure A above and using 2-aminonaphthalene (Aldrich) and isobutyl pyruvate (prepared by following General Procedure O above), the title compound was prepared as an oil. Purification was by preparative plate chromatography (silica gel using 25% EtOAc/hexanes as the eluant).

NMR data was as follows:

$^1$H-nmr (CDCl$_3$): δ=7.65 (m, 3H), 7.38 (t, 1H, J=6.9 Hz), 7.23 (t, 1H, J=6.9 Hz), 6.93 (m, 1H), 6.81 (d, 1H, J=2.3 Hz), 4.31 (q, 1H, J=6.9 Hz), 3.95 J=6.7 Hz, J=1.6 Hz), 1.96 (sept, 1H, J=6.7 Hz), 1.57 (d, 3H, J=6.9 Hz), 0.93 (dd, 6H, J=6.7 Hz, J=1.6 Hz).

$^{13}$C-nmr (CDCl$_3$) δ=174.6, 144.2, 134.9, 129.1, 127.8, 127.6, 126.3, 126.0, 122.3, 118.1, 105.3, 71.2, 52.0, 27.7, 18.9, 18.8.

Example 41

Synthesis of N-(2-methylquinolin-6-yl)alanine iso-butyl ester

Following General Procedure A above and using 6-amino-2-methylquinoline (Lancaster) and iso-butyl pyruvate (prepared by following General Procedure O above), the title compound was prepared. The reaction was monitored by silica gel tlc (Rf=0.44 in 50% EtOAc/hexanes). Purification was by flash chromatography (silica gel using 50% EtOAc/hexanes as the eluant).

NMR data was as follows:

$^1$H-nmr (CDCl$_3$): δ=7.90 (m, 2H), 7.10 (m, 2H), 6.66 (d, 1H, J=2.6), 4.50 (bd, 1H), 4.24 (m, 1H), 3.91 (d, 2H, J=6.6 Hz), 2.64 (s, 3H), 1.91 (sept, 1H, J=6.7 Hz), 1.52 (d, 3H, J=6.9 Hz), 0.87 (d, 6H, J=6.7 Hz).

$^{13}$C-nmr (CDCl$_3$) δ=175.0, 155.4, 144.6, 143.4, 134.9, 130.2, 128.4, 122.8, 121.8, 104.9, 71.8, 52.7, 28.3, 25.4, 19.5, 19.4.

$C_{17}H_{22}Cl_2N_2O_2$ (MW=286.38); mass spectroscopy (MH$^+$) 287.

Example 42

Synthesis of N-(3,4-methylenedioxyphenyl)alanine iso-butyl ester

Following reductive amination General Procedure A above and using 3,4-methylenedioxyaniline (Aldrich) and methyl pyruvate (Aldrich), N-(3,4-methylenedioxyphenyl) alanine methyl ester was prepared. The methyl ester was then transesterified following General Procedure Q above and using iso-butanol to provide the title compound as an oil. The reaction was monitored by silica gel tlc (Rf=0.61 in 25% EtOAc/hexanes). Purification was by preparative plate chromatography with silica gel using 25% EtOAc/hexanes as the eluant.

NMR data was as follows:

$^1$H-nmr (CDCl$_3$): δ=6.63 (d, 1H, 8.3 Hz), 6.25 (d, 1H, J=2.3 Hz), 6.04 (dd, 1H, J=8.3 Hz, J=2.3 Hz), 5.83 (s, 2H), 3.96 (m, 4H), 1.92 (sept, 1H, J=6.7 Hz), 1.44 (d, 3H, J=6.9 Hz), 0.90 (d, 6H, J=6.6 Hz).

$^{13}$C-nmr (CDCl$_3$): δ=175.4, 148.9, 142.9, 140.8, 109.2, 105.8, 101.2, 97.4, 71.6, 53.6, 28.3, 19.6, 19.5.

$C_{14}H_{19}NO_4$ (MW=265.31); mass spectroscopy (MH$^+$) 265.

Example 43

Synthesis of N-(3,4-ethylenedioxyphenyl)alanine iso-butyl ester

Following reductive amination General Procedure A above and using 1,4-benzodioxa-6-amine (Aldrich) and methyl pyruvate (Aldrich), N-(3,4-ethylenedioxyphenyl) alanine methyl ester was prepared. The methyl ester was then transesterified following General Procedure Q above using isobutanol to provide the title compound. Purification was by preparative plate chromatography.

NMR data was as follows:

$^1$H-nmr (CDCl$_3$): δ=0.91 (d, J=7 Hz, 6H), 1.42 (d, J=7 Hz, 3H), 1.8–2.0 (m, 1H), 3.8–3.95 (m, 3H), 4.0–4.1 (m, 1H), 4.15–4.25 (m, 4H), 6.12–6.2 (m, 2H), 6.65–6.75 (m, 1H).

$^{13}$C-nmr (CDCl$_3$): δ=19.55, 19.56, 19.67, 28.3, 53.4, 64.7, 65.3, 71.7, 103.1, 108.0, 118.3, 142.1, 144.6, 175.4.

$C_{15}H_{21}NO_4$ (MW=279.34); mass spectroscopy (MH$^+$) 280.

Example 44

Synthesis of N-(2-naphthyl)alanine methyl ester

Following reductive amination General Procedure A above and using 2-aminonaphthalene (Aldrich) and methyl pyruvate (Aldrich), the title compound was prepared. The reaction was monitored by silica gel tlc (Rf=0.50 in 25% EtOAc/hexanes). Purification was by flash chromatography with silica gel using 25% EtOAc/hexanes as the eluant.

NMR data was as follows:

$^1$H-nmr (CDCl$_3$): δ=7.65 (m, 3H), 7.48 (m, 1H), 7.25 (m, 1H), 6.91 (m, 1H), 6.79 (m, 1H), 4.31 (m, 2H), 3.76 (s, 3H), 1.55 (d, 3H).

$^{13}$C-nmr (CDCl$_3$): δ=175.66, 144.78, 135.55, 129.78, 128.47, 128.22, 126.96, 126.67, 123.01, 118.66, 105.88, 52.95, 52.51, 19.45.

$C_{14}H_{15}NO_2$ (MW=229.28); mass spectroscopy (MH$^+$) 229.

Example 45

Synthesis of N-(benzothiazol-6-yl)alanine ethyl ester

To a solution of 6-aminobenzothiazole (Lancaster) in dichloromethane was added 1.2 equivalents of pyridine, followed by 1.5 equivalents of trifluoroacetic anhydride. The reaction was stirred at room temperature for 3 hours and then washed with 5% citric acid, dried over $MgSO_4$, and stripped free of solvent on a rotary evaporator to yield 6-trifluoroacetamidothiazole. This material was dissolved in THF and then added to a suspension of KH in THF at 0° C. A catalytic amount of 18-crown-6 was added, followed by ethyl 2-bromopropionate (Aldrich). The reaction was held at room temperature for 1 hour, and then heated to reflux for 24 hours, and then cooled to room temperature. The reaction mixture was stripped free of solvent on a rotary evaporator and the resulting residue was dissolved in ether. This solution was washed with water, saturated aqueous NaCl, and dried over $MgSO_4$. The solution was stripped free of solvent on a rotary evaporator and the title compound was obtained by chromatography of the residue using 5% methanol/dichloromethane (Rf=0.59) as the eluant.

NMR data was as follows:

$^1$H-nmr (CDCl$_3$): δ=8.69 (s, 1H), 7.90 (d, 1H, J=8.8 Hz), 7.04 (d, 1H, J=2.3 Hz), 6.84 (dd, 1H, J=8.8 Hz, J=2.4 Hz), 4.41 (bd, 1H, J=7.5 Hz), 4.20 (m, 3H), 1.53 (d, 3H, J=6.9 Hz), 1.27 (t, 3H, J=7.1 Hz).

$^{13}$C-nmr (CDCl$_3$): δ=174.9, 150.2, 147.1, 145.6, 136.3, 124.6, 115.7, 103.5, 61.9, 52.9, 19.4, 14.8.

$C_{12}H_{14}N_2O_2S$ (MW=250.32); mass spectroscopy (MH$^+$) 251.

Example 46

Synthesis of N-(indol-5-yl)alanine iso-butyl ester (S isomer)

Following General Procedure M and using 5-aminoindole (Aldrich) and iso-butyl R-(+)-lactate (Aldrich), the title compound was prepared as an oil. The reaction was monitored by silica gel tlc (Rf=0.46 in 33% EtOAc/hexanes). Purification was by preparative plate chromatography with silica gel using 33% EtOAc/hexanes as the eluant.

NMR data was as follows:

$^1$H-nmr (CDCl$_3$): δ=8.11 (bs, 1H), 7.07 (d, J=8.8 Hz, 1H), 6.98 (d, J=2.8 Hz, 1H), 6.83 (d, J=2.2 Hz, 1H), 6.61 (m, 1H), 6.32 (m, 1H), 4.18 (q, J=6.9 Hz, 1H), 3.95 (bs, 1H), 3.87 (d, J=6.7 Hz, 2H), 1.89 (hept, J=6.7 Hz, 1H), 1.48 (d, J=6.96 Hz, 3H), 0.86 (dd, J=6.7 Hz, J=1.6 Hz, 6H).

$^{13}$C-nmr (CDCl$_3$): δ=176.15, 141.06, 131.28, 129.24, 125.34, 113.34, 112.53, 104.21, 102.17, 71.65, 54.28, 28.36, 19.87, 19.62.

$C_{15}H_{20}N_2O_2$ (MW=260.34); mass spectroscopy (MH$^+$) 261.

Example 47

Synthesis of N-(naphth-2-yl)alanine O-acylacetamidoxime ester

Following General Procedure I above using N-(naphth-2-yl)alanine 2,4,6-trichlorophenyl ester (from Example E above) and acetamide oxime (prepared according to the procedures described in *J. Org. Chem.*, 46, 3953 (1981)), the title compound was prepared as a semisolid. The reaction was monitored by tlc on silica gel (Rf=0.4 in ethyl acetate) and purification was by preparative plate chromatography (silica gel using ethyl acetate as the eluant).

NMR data was as follows:

$^1$H-nmr (d$^6$-DMSO): δ=7.64 (t, 2H), 7.54 (d, 1H), 7.32 (t, 1H), 7.13 (t, 1H), 7.04 (d, 1H), 6.78 (s, 1H) 6.42 (broad s, 2H), 6.32 (d, 1H), 4.33 (m, 1H), 1.72 (s, 3H), 1.46 (d, 3H).

$C_{15}H_{17}N_3O_2$ (MW=271.32); mass spectroscopy: 271.

Example 48

Synthesis of N-(2-naphthyl)alanine ethyl ester

Following reductive amination General Procedure A above and using 2-aminonaphthalene (Aldrich) and ethyl pyruvate (Aldrich), the title compound was prepared as a solid having a melting point of 52–56° C. The reaction was monitored by silica gel tlc (Rf=0.50 in 25% EtOAc/hexanes). Purification was by flash chromatography with silica gel using 25% EtOAc/hexanes as the eluant.

NMR data was as follows:

$^1$H-nmr (CDCl$_3$): δ=7.65 (m, 3H), 7.48 (m, 1H), 7.25 (m, 1H), 6.91 (m, 1H), 6.79 (m, 1H), 4.31 (m, 2H), 3.76 (s, 3H), 1.55 (d, 3H).

$^{13}$C-nmr (CDCl$_3$): δ=175.66, 144.78, 135.55, 129.78, 128.47, 128.22, 126.96, 126.67, 123.01, 118.66, 105.88, 52.95, 52.51, 19.45.

$C_{14}H_{15}NO_2$ (MW=229.28); mass spectroscopy (MH$^+$) 229.

Example 49

Synthesis of N-(3,4-dichlorophenyl)alanine O-acylpropionamidoxime ester

Following General Procedure I above using N-(3,4-dichlorophenyl)alanine 2,4,6-trichlorophenyl ester (prepared from N-(3,4-dichlorophenyl)alanine methyl ester (from Example 9) using essentially the same procedure as described in Example E above) and propionamide oxime (prepared according to the procedures described in *J. Org. Chem.*, 46, 3953 (1981)), the title compound was prepared as a semisolid. The reaction was monitored by tlc on silica gel (Rf=0.2 in 50% ethyl acetate/hexane) and purification was by preparative plate chromatography (silica gel using 50% ethyl acetate/hexane as the eluant).

NMR data was as follows:

$^1$H-nmr (d$^6$-DMSO): δ=7.27 (d, 1H), 6.83 (s, 1H), 6.64 (d, 1H), 6.47 (d, 1H), 6.38 (broad s, 2H), 4.24 (m, 1H), 2.07 (q, 2H), 1.41 (d, 3H).

$C_{12}H_{15}Cl_2N_3O_2$ (MW=304.17); mass spectroscopy (MH$^+$) 305.

Example 50

Synthesis of N-(4-ethoxycarbonylphenyl)alanine iso-butyl ester (S isomer)

Following General Procedure M and using ethyl 4-aminobenzoate (Aldrich) and iso-butyl R-(+)-lactate (Aldrich), the title compound was prepared as an oil. The reaction was monitored by silica gel tlc (Rf=0.21 in 10% EtOAc/hexanes). Purification was by preparative plate thin layer chromatography using 25% EtOAc/hexanes as the eluant.

NMR data was as follows:

$^1$H-nmr (CDCl$_3$): δ=7.82 (d, J=8.73 Hz, 2H), 6.51 (d, J=8.79 Hz, 2H), 4.81 (d, J=7.82 Hz, 1H), 4.25 (q, J=7.14 Hz, 2H), 4.15 (quint, J=7.40 Hz, 1H), 3.87 (m, 2H), 1.87 (sept, J=6.70 Hz, 1H), 1.43 (d, J=6.95 Hz, 3H), 1.30 (t, J=7.14 Hz, 3H), 0.84 (d, J=6.71 Hz, 6H).

$^{13}$C-nmr (CDCl$_3$): δ=174.5, 167.3, 151.0, 132.0, 119.9, 112.5, 71.9, 60.8, 51.9, 28.2, 19.5, 19.2, 15.0.

$C_{16}H_{23}NO_4$ (MW=293.37); mass spectroscopy (MH$^+$) 294.

Example 51

Synthesis of N-[3,5-di(trifluoromethyl)phenyl] alanine iso-butyl ester (S isomer)

Following General Procedure M and using 3,5-di (trifluoromethyl)aniline (Aldrich) and iso-butyl R-(+)-lactate (Aldrich), the title compound was prepared as an oil. The reaction was monitored by silica gel tlc (Rf=0.38 in 10% EtOAc/hexanes). Purification was by preparative plate thin layer chromatography using 10% EtOAc/hexanes as the eluant.

NMR data was as follows:

$^1$H-nmr (CDCl$_3$): δ=7.13 (s, 1H), 6.91 (s, 2H), 4.97 (d, J=8.24 Hz, 1H), 4.18 (m, 1H), 3.93 (d, J=6.59 Hz, 2H), 1.93 (sept, J=6.71 Hz, 1H), 1.49 (d, J=7.02 Hz, 3H), 0.89 (d, J=6.59 Hz, 6H).

$^{13}$C-nmr (CDCl$_3$): δ=174.4, 147.9, 133.6, 133.2, 132.7, 132.3, 129.4, 125.8, 122.2, 118.6, 112.81, 112.76, 111.42, 111.37, 111.32, 111.27, 111.22, 72.2, 52.0, 32.1, 28.24, 28.17, 23.2, 19.5, 19.3, 19.2, 18.9, 14.6.

$C_{15}H_{17}F_6NO_2$ (MW=357.30); mass spectroscopy (MH$^+$) 358.

Example 52

Synthesis of N-(3,5-dimethoxyphenyl)alanine iso-butyl ester

N-(3,5-dimethoxyphenyl)alanine (crude, 454 mg) (prepared according to the procedure described in U.S. Pat. No. 3,598,859 using 3,5-dimethoxyaniline (Aldrich) and 2-chloropropionic acid (Aldrich)) was treated in dry iso-butanol (10 mL) with 0.1 mL of chlorotrimethylsilane and the reaction mixture refluxed overnight. The excess alcohol was removed at reduced pressure and the residue dissolved in ethyl acetate. The ethyl acetate solution was washed with saturated aqueous NaHCO$_3$, dried with Na$_2$SO$_4$ and the solvent removed to provide the title compound. The reaction was monitored by silica gel tlc (Rf=0.3 in 20% EtOAc/hexanes). Purification was by preparative thin layer chromatography using 20% EtOAc/hexanes as the eluant.

NMR data was as follows:

$^1$H-nmr (CDCl$_3$): δ=0.9 (d, J=7, 6H), 1.47 (d, J=7, 3H), 1.9–2.0 (m, 1H), 3.7 (s, 6H), 3.85–4.0 (m, 2H), 4.1–4.2 (m, 1H), 4.3 (brs, 1H), 5.8 (s, 2H), 5.9 (s, 1H).

$^{13}$C-nmr (CDCl$_3$): δ=19.49, 19.52, 19.54, 28.3, 52.5, 55.6, 71.7, 91.1, 92.7, 149.2, 162.3, 175.2.

$C_{15}H_{23}NO_4$ (MW=281.35).

Example 53

Synthesis of N-(2-napthyl)alanine O-acylpropionamidoxime ester

Following General Procedure S and using N-(2-naphthyl) alanine 2,4,5-trichlorophenyl ester (from Example E above) and propionamide oxime (prepared according to the procedures described in J. Org. Chem., 46, 3953 (1981)), the title compound was prepared. The reaction was monitored by silica gel tlc (Rf=0.5 in EtOAc). Purification was by silica gel chromatography using 1:1 EtOAc/hexanes as the eluant.

NMR data was as follows:

$^1$H-nmr (DMSO-d$_6$): δ=1.03 (t, 3H), 1.45 (d, 3H).

$C_{16}H_{19}N_3O_2$ (MW=285.35); mass spectroscopy (M$^+$) 285.

Example 54

Synthesis of N-(2-napthyl)alanine O-acylbutyramidoxime ester

Following General Procedure S and using N-(2-naphthyl) alanine 2,4,5-trichlorophenyl ester (from Example E above) and butyramide oxime prepared according to the procedures described in J. Org. Chem., 46, 3953 (1981)), the title compound was prepared as an oil. The reaction was monitored by silica gel tlc (Rf=0.6 in EtOAc). Purification was by silica gel chromatography using 1:1 EtOAc/hexanes as the eluant.

NMR data was as follows:

$^1$H-nmr (DMSO-d$_6$): δ=0.86 (t, 3H), 1.46 (d, 3H).

$C_{17}H_{21}N_3O_2$ (MW=299.37); mass spectroscopy (MH$^+$) 299.

Example 55

Synthesis of N-(2-napthyl)alanine O-acylisovaleramidoxime ester

Following General Procedure S and using N-(2-naphthyl) alanine 2,4,5-trichlorophenyl ester (from Example E above) and isovaleramide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=0.86 (t, 3H), 1.45 (d, 3H).

$C_{18}H_{23}N_3O_2$ (MW=313.40); mass spectroscopy (MH$^+$) 313.

Example 56

Synthesis of N-(2-napthyl)alanine O-acylbenzamidoxime ester

Following General Procedure S and using N-(2-naphthyl) alanine 2,4,5-trichlorophenyl ester (from Example E above) and benzamide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=4.42 (m, 1H), 1.53 (d, 3H).

$C_{20}H_{19}N_3O_2$ (MW=333.39); mass spectroscopy (MH$^+$) 333.

Example 57

Synthesis of N-(2-napthyl)alanine O-acylcyclopropanecarboxamidoxime ester

Following General Procedure S and using N-(2-naphthyl) alanine 2,4,5-trichlorophenyl ester (from Example E above)

and cyclopropanecarboxamide oxime (prepared according to the procedures described in *J. Org. Chem.,* 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=0.85 (m, 4H), 1.43 (d, 3H).

$C_{17}H_{19}N_3O_2$ (MW=297.36); mass spectroscopy (MH$^+$) 297.

Example 58

Synthesis of N-(2-napthyl)alanine O-acylcyclopropylacetamidoxime ester

Following General Procedure S and using N-(2-naphthyl) alanine 2,4,5-trichlorophenyl ester (from Example E above) and cyclopropylacetamide oxime (prepared according to the procedures described in *J. Org. Chem.,* 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=1.43 (d, 3H), 1.91 (d, 2H).

$C_{18}H_{21}N_3O_2$ (MW=311.39); mass spectroscopy (MH$^+$) 311.

Example 59

Synthesis of N-(2-napthyl)alanine O-acylcyclopentanecarboxamidoxime ester

Following General Procedure S and using N-(2-naphthyl) alanine 2,4,5-trichlorophenyl ester (from Example E above) and cyclopentanecarboxamide oxime (prepared according to the procedures described in *J. Org. Chem.,* 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=1.43 (d, 3H), 2.43 (m, 1H).

$C_{17}H_{19}N_3O_2$ (MW=297.36).

Example 60

Cellular Screen for the Detection of Inhibitors of β-Amyloid Production

Numerous compounds of formula I above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation Lys$_{651}$Met$_{652}$ to Asn$_{651}$Leu$_{652}$ (APP751 numbering) in the manner described in International Patent Application Publication No. 94/10569[8] and Citron et al.[12]. This mutation is commonly called the Swedish mutation and the cells, designated as "293 751 SWE", were plated in Corning 96-well plates at 1.5–2.5×10$^4$ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266 [P. Seubert, *Nature* (1992) 359:325–327] against amino acids 13–28 of β-amyloid peptide as described in International Patent Application Publication No. 94/10569[8] and stored at 4° C. overnight. An ELISA assay employing labelled antibody 6C6 [P. Seubert, *Nature* (1992) 359:325–327] against amino acids 1–16 of β-amyloid peptide was run the next day to measure the amount of β-amyloid peptide produced.

Cytotoxic effects of the compounds were measured by a modification of the method of Hansen, et al.[13]. To the cells remaining in the tissue culture plate was added 25 μL of a 3-(4,5-dimethylthiazol-2-yl)-2,5-diphenyltetrarolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the OD$_{562\ nm}$ and the OD$_{650\ nm}$ was measured in a Molecular Device's UV$_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that, each of the compounds of Examples 1–59 inhibit the β-amyloid peptide production by at least 30% as compared to control.

Example 61

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) *Nature* 373:523–527]. Depending upon which compound is being tested, the compound is usually formulated at either 5 or 10 mg/ml. Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxy-methyl-cellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25 G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/ml aprotinin, 5 mM EDTA, pH 8.0, 10 μg/ml leupeptin], thereby reducing the final concentration of guanidine to 0.5 M, before centrifugation at 16,000×g for 20 minutes at 4° C. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266 [P. Seubert, Nature (1992) 359:325–327], is specific to amino acids 13–28 of β-amyloid. The antibody 3D6 [Johnson-Wood et al., PNAS USA (1997) 94:1550–1555], which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1–42) employs the mAb 21F12 [Johnson-Wood et al., PNAS USA (1997) 94:1550–1555] (which recognizes amino acids 33–42 of β-amyloid) as the capture antibody. Biotinylated 3D6 is also the reporter antibody in this assay which has a lower limit of sensitivity of ~125 pg/ml (28 pM).

The 266 and 21F12 capture mAbs are coated at 10 μg/ml into 96 well immunoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

From the foregoing description, various modifications and changes in the composition and method will occur to those skilled in the art. All such modifications coming within the scope of the appended claims are intended to be included therein.

What is claimed is:

1. A pharmaceutical composition comprising a pharmaceutically inert carrier and a pharmaceutically effective amount of a compound of formula I:

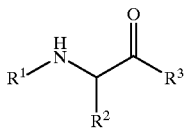

I wherein
$R^1$ is selected from the group consisting of:
(a) a substituted phenyl group of formula II:

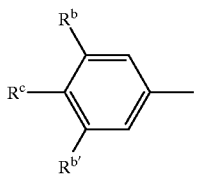

II wherein
$R^c$ is selected from the group consisting of acyl, alkyl, alkoxy, alkoxycarbonyl, alkylalkoxy, azido, cyano, halo, hydrogen, nitro, trihalomethyl, thioalkoxy, and where $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
$R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
(b) 2-naphthyl; and
(c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;
$R^2$ is selected from the group consisting of hydrogen, alkyl of from 1 to 4 carbon atoms, alkylalkoxy of from 1 to 4 carbon atoms and alkylthioalkoxy of from 1 to 4 carbon atoms; and
$R^3$ is selected from the group consisting of:
(a) —Y(CH$_2$)$_n$CHR$^4$R$^5$ wherein n is an integer of from 0 to 2, Y is selected from the group consisting of oxygen and sulfur, $R^4$ and $R^5$ are independently selected from the group consisting of hydrogen, alkyl, alkenyl, aryl optionally substituted with from 1 to 3 substituents selected from the group consisting of alkyl, alkoxy, halo, cyano, nitro, trihalomethyl, and thioalkoxy, heteroaryl optionally substituted with from 1 to 3 substituents selected from the group consisting of alkyl, alkoxy, halo, cyano, nitro, trihalomethyl, and thioalkoxy, and where $R^4$ and $R^5$ are joined to form a cycloalkyl group, a cycloalkenyl group or a heterocyclic group;
(b) —ON=C(NH$_2$)R$^6$ where $R^6$ is selected from the group consisting of alkyl, aryl, cycloalkyl, and heteroaryl;
(c) —O(CH$_2$)$_p$C(O)OR$^7$ wherein p is an integer of from 1 to 2 and $R^7$ is alkyl; and
(d) —NR$^8$R$^9$ wherein $R^8$ and $R^9$ are joined to form a pyrrolyl group;
and pharmaceutically acceptable salts thereof
with the provisos that
1. when $R^1$ is the substituted phenyl group of formula II above, $R^{b'}$ is hydrogen, $R^b$ and $R^c$ are chloro, and $R^2$ is methyl, then $R^3$ is not —OCH(CH$_3$)—φ;
2. when $R^1$ is the substituted phenyl group of formula II above, when $R^{b'}$ is hydrogen, $R^b$ and $R^c$ are chloro, and $R^3$ is —OCH$_2$CH$_3$ then $R^2$ is not hydrogen;
3. when $R^1$ is the substituted phenyl group of formula II above, $R^{b'}$ is hydrogen, $R^b$ and $R^c$ are chloro, and $R^3$ is —OCH$_2$CH(CH$_3$)$_2$ then $R^2$ is not —CH(CH$_3$)CH$_2$CH$_3$; and
4. when $R^1$ is N-methylindol-5-yl and $R^2$ is methyl, then $R^3$ is not —OCH$_2$CH$_3$.

2. The pharmaceutical composition according to claim 1 wherein $R^1$ is selected from the group consisting of 4-substituted, 3,5-disubstituted or 3,4-disubstituted phenyl substituents wherein the substituents at the 3 and/or 5 positions are defined by $R^b$, $R^{b'}$ as above and the substituent at the 4 position is defined by $R^c$ as above.

3. The pharmaceutical composition according to claim 2 wherein $R^1$ is a 3,5-disubstituted phenyl selected from the group consisting of 3,5-dichlorophenyl, 3,5-difluorophenyl, 3,5-di(trifluoromethyl)phenyl and 3,5-dimethoxyphenyl.

4. The pharmaceutical composition according to claim 2 wherein $R^1$ is a 3,4-disubstituted phenyl selected from the group consisting of 3,4-dichlorophenyl, 3,4-difluorophenyl, 3-(trifluoromethyl)-4-chlorophenyl, 3-chloro-4-cyanophenyl, 3-chloro-4-iodophenyl, 3,4-ethylenedioxyphenyl, and 3,4-methylenedioxyphenyl.

5. The pharmaceutical composition according to claim 2 wherein $R^1$ is a 4-substituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, 4-(1-ethoxy)ethylphenyl, and 4-(ethoxycarbonyl)phenyl.

6. The pharmaceutical composition according to claim 1 wherein $R^1$ is selected from the group consisting of 2-naphthyl, 2-methylquinolin-6-yl, benzothiazol-6-yl and 5-indolyl.

7. The pharmaceutical composition according to claim 1 wherein $R^2$ is selected from the group consisting of alkyl of from 1 to 4 carbon atoms, alkylalkoxy of from 1 to 4 carbon atoms and alkylthioalkoxy of from 1 to 4 carbon atoms.

8. The pharmaceutical composition according to claim 7 wherein $R^2$ is selected from the group consisting of methyl, ethyl, n-propyl and iso-butyl.

9. The pharmaceutical composition according to claim 1 wherein $R^3$ is selected from the group consisting of methoxy, ethoxy, iso-propoxy, n-propoxy, n-butoxy, iso-butoxy, cyclopentoxy, allyloxy, 4-methylpentoxy, —O—CH$_2$—(2,2-dimethyl-1,3-dioxolan-4-yl), —O—CH$_2$-cyclohexyl, —O—CH$_2$-(3-tetrahydrofuranyl), —O—CH$_2$—C(O)O-tert-butyl, —O—CH$_2$—C(CH$_3$)$_3$, —O—CH$_2$—φ, —OCH$_2$CH(CH$_2$CH$_3$)$_2$, —O(CH$_2$)$_3$CH(CH$_3$)$_2$, —ON═C(NH$_2$)φ, —ON═C(NH$_2$)CH$_3$, —ON═C(NH$_2$)CH$_2$CH$_3$, —ON═C(NH$_2$)CH$_2$CH$_2$CH$_3$, —ON═C(NH$_2$)-cyclopropyl, —ON═C(NH$_2$)—CH$_2$-cyclopropyl, —ON═C(NH$_2$)-cyclopentyl, and —ON═C(NH$_2$)CH$_2$CH(CH$_3$)$_2$.

10. The pharmaceutical composition according to claim 1 wherein the compound of formula I is selected from the group consisting of:

N-(3,4-dichlorophenyl)alanine ethyl ester;
N-(3-trifluoromethyl-4-chlorophenyl)alanine ethyl ester;
N-(3,5-dichlorophenyl)alanine ethyl ester;
N-(3,4-difluorophenyl)alanine ethyl ester;
N-(3,4-dichlorophenyl)alanine benzyl ester;
N-(3,4-dichlorophenyl)alanine iso-butyl ester;
N-(3,4-dichlorophenyl)alanine iso-propyl ester;
N-(3,4-dichlorophenyl)alanine n-butyl ester;
N-(3,4-dichlorophenyl)alanine methyl ester;
N-(3,4-dichlorophenyl)alanine cyclopentyl ester;
N-(3,4-dichlorophenyl)alanine n-propyl ester;
N-(3,4-dichlorophenyl)alanine allyl ester;
N-(3,4-dichlorophenyl)alanine 4-methylpentyl ester;
N-(3,4-dichlorophenyl)alanine 2,2-dimethyl-1,3-dioxolane-4-methyl ester;
N-(3,4-dichlorophenyl)alanine cyclohexylmethyl ester;
N-(3,4-dichlorophenyl)alanine tert-butoxycarbonylmethyl ester;
N-(3,4-dichlorophenyl)leucine iso-butyl ester;
2-[N-(3,4-dichlorophenyl)amino]pentanoic acid iso-butyl ester;
N-(4-cyanophenyl)alanine iso-butyl ester;
N-(3-chloro-4-cyanophenyl)alanine iso-butyl ester;
N-(3,4-dichlorophenyl)alanine tetrahydrofuran-3-yl-methyl ester;
N-(3-chloro-4-iodophenyl)alanine iso-butyl ester;
2-[N-(3,4-dichlorophenyl)amino]butanoic acid iso-butyl ester;
N-(4-chlorophenyl)alanine iso-butyl ester;
N-(3,5-dichlorophenyl)alanine iso-butyl ester;
N-(4-ethylphenyl)alanine methyl ester;
N-[4-(1-ethoxy)ethylphenyl]alanine methyl ester;
N-(3,4-dichlorophenyl)alanine 2,2-dimethylpropyl ester;
N-(3,4-dichlorophenyl)glycine iso-butyl ester;
N-(3,4-dichlorophenyl)alanine 2-ethylbuty ester;
N-(3-chloro-4-iodophenyl)alanine iso-butyl ester;
N-(4-azidophenyl)alanine iso-butyl ester;
N-[(4-phenylcarbonyl)phenyl]alanine iso-butyl ester;
N-(3,5-difluorophenyl)alanine iso-butyl ester;
N-(3,4-dichlorophenyl)alanine O-acylacetamidoxime ester;
N-(3,4-dichlorophenyl)alanine pyrrolyl amide;
N-(3,4-dichlorophenyl)alanine O-acylpropionamideoxime ester;
N-(3,4-dichlorophenyl)alanine O-acylbutyramideoxime ester;
2-[N-(naphth-2-yl)amino]butanoic acid ethyl ester;
N-(naphth-2-yl)alanine iso-butyl ester;
N-(2-methylquinolin-6-yl)alanine iso-butyl ester;
N-(3,4-ethylenedioxyphenyl)alanine iso-butyl ester;
N-(3,4-methylenedioxyphenyl)alanine iso-butyl ester;
N-(naphth-2-yl)alanine methyl ester;
N-(benzothiazol-6-yl)alanine ethyl ester;
N-(indol-5-yl)alanine iso-butyl ester;
N-(naphth-2-yl)alanine O-acylacetamidoxime ester;
N-(2-naphthyl)alanine ethyl ester;
N-(4-ethoxycarbonylphenyl)alanine iso-butyl ester;
N-(3,5-di(trifluoromethyl)phenyl)alanine iso-butyl ester;
N-(3,5-dimethoxyphenyl)alanine iso-butyl ester;
N-(2-napthyl)alanine O-acylpropionamidoxime ester;
N-(2-napthyl)alanine O-acylbutyramidoxime ester;
N-(2-napthyl)alanine O-acylisovaleramidoxime ester;
N-(2-napthyl)alanine O-acylbenzamidoxime ester;
N-(2-napthyl)alanine O-acylcyclopropanecarboxamidoxime ester;
N-(2-napthyl)alanine O-acylcyclopropylacetamidoxime ester; and
N-(2-napthyl)alanine O-acylcyclopentanecarboxamidoxime ester.

11. A compound of formula III:

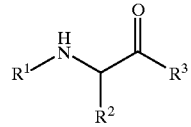

III wherein
$R^1$ is selected from the group consisting of:
(a) a substituted phenyl group of formula II:

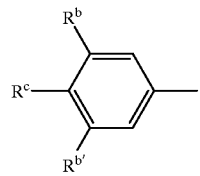

II wherein
$R^c$ is selected from the group consisting of acyl, alkyl, alkoxy, alkoxycarbonyl, alkylalkoxy, azido, cyano, halo, hydrogen, nitro, trihalomethyl, thioalkoxy, and where $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
$R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
(b) 2-naphthyl; and
(c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;
$R^2$ is selected from the group consisting of alkyl of from 1 to 4 carbon atoms, alkylalkoxy of from 1 to 4 carbon atoms and alkylthioalkoxy of from 1 to 4 carbon atoms; and $R^3$ is selected from the group consisting of:
- (a) —Y(CH$_2$)$_n$CHR$^4$R$^5$ wherein n is an integer of from 0 to 2, Y is selected from the group consisting of oxygen and sulfur, R$^4$ and R$^5$ are independently selected from the group consisting of hydrogen, alkyl, alkenyl, aryl optionally substituted with from 1 to 3 substituents selected from the group consisting of alkyl, alkoxy, halo, cyano, nitro, trihalomethyl, and thioalkoxy, heteroaryl optionally substituted with from 1 to 3 substituents selected from the group consisting of alkyl, alkoxy, halo, cyano, nitro, trihalomethyl, and thioalkoxy, and where R$^4$ and R$^5$ are joined to form a cycloalkyl group, a cycloalkenyl group or a heterocyclic group;
- (b) —ON=C(NH$_2$)R$^6$ where R$^6$ is selected from the group consisting of alkyl, aryl, cycloalkyl, and heteroaryl;
- (c) —O(CH$_2$)$_p$C(O)OR$^7$ wherein p is an integer of from 1 to 2 and R$^7$ is alkyl;
- (d) —NR$^8$R$^9$ wherein R$^8$ and R$^9$ are joined to form a pyrrolyl group;

and pharmaceutically acceptable salts thereof
with the proviso excluding the following compounds:
1. when R$^1$ is the substituted phenyl group of formula II above, R$^{b'}$ is hydrogen, R$^b$ and R$^c$ are chloro, and R$^2$ is methyl, then R$^3$ is not —OCH(CH$_3$)—φ;
2. when R$^1$ is the substituted phenyl group of formula II above, when R$^{b'}$ is hydrogen, R$^b$ and R$^c$ are chloro, and R$^3$ is —OCH$_2$CH$_3$ then R$^2$ is not hydrogen;
3. when R$^1$ is the substituted phenyl group of formula II above, R$^{b'}$ is hydrogen, R$^b$ and R$^c$ are chloro, and R$^3$ is —OCH$_2$CH(CH$_3$)$_2$ then R$^2$ is not —CH(CH$_3$)CH$_2$CH$_3$;
4. when R$^1$ is a substituted phenyl group of the formula:

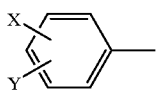

wherein X is hydrogen, halogen or methyl and Y is halogen or methyl, then R$^2$ is not hydrogen or methyl;
5. when R$^1$ is 2-napthyl or a 6-methoxy-substituted 2-naphthyl and R$^2$ is methyl then R$^3$ is not —OCH$_2$CH$_3$; and
6. when R$^1$ is N-methylindol-5-yl and R$^2$ is methyl, then R$^3$ is not —OCH$_2$CH$_3$;

and still with further proviso excluding the following known compounds:

N-(4-chlorophenyl)alanine ethyl ester;
N-(3,4-dichlorophenyl)alanine ethyl ester;
N-(3,5-dichlorophenyl)alanine ethyl ester;
N-(4-n-butylphenyl)alanine ethyl ester;
N-(3,4-dinitrophenyl)alanine ethyl ester;
N-(4-chlorophenyl)glycine heptenyl ester;
N-(4-methylphenyl)glycine butyl ester;
N-(3-nitrophenyl)glycine decyl ester;
N-(3,4-difluorophenyl)alanine methyl ester;
N-(3,4-difluorophenyl)alanine ethyl ester;
N-(3,4-difluorophenyl)alanine iso-propyl ester;
N-(4-fluorophenyl)alanine ethyl ester;
N-(3-chloro-4-fluorophenyl)alanine methyl ester;
N-(3-chloro-4-fluorophenyl)alanine ethyl ester; and
N-(3-chloro-4-fluorophenyl)alanine iso-propyl ester.

12. The compound according to claim 11 wherein R$^1$ is selected from the group consisting of 4-substituted, 3,5-disubstituted or 3,4-disubstituted phenyl substituents wherein the substituents at the 3 and/or 5 positions are defined by R$^b$, R$^{b'}$ as above and the substituent at the 4 position is defined by R$^c$ as above.

13. The compound according to claim 12 wherein R$^1$ is a 3,5-disubstituted phenyl selected from the group consisting of 3,5-dichlorophenyl, 3,5-difluorophenyl, 3,5-di(trifluoromethyl)phenyl and 3,5-dimethoxyphenyl.

14. The compound according to claim 11 wherein R$^1$ is a 3,4-disubstituted phenyl selected from the group consisting of 3,4-dichlorophenyl, 3,4-difluorophenyl, 3-(trifluoromethyl)-4-chlorophenyl, 3-chloro-4-cyanophenyl, 3-chloro-4-iodophenyl, 3,4-ethylenedioxyphenyl, and 3,4-methylenedioxyphenyl.

15. The compound according to claim 11 wherein R$^1$ is a 4-substituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, 4-(1-ethoxy)ethylphenyl, and 4-(ethoxy-carbonyl)phenyl.

16. The compound according to claim 11 wherein R$^1$ is selected from the group consisting of 2-naphthyl, 2-methylquinolin-6-yl, benzothiazol-6-yl and 5-indolyl.

17. The compound according to claim 11 wherein R$^2$ is selected from the group consisting of methyl, ethyl, n-propyl and iso-butyl.

18. The compound according to claim 11 wherein R$^3$ is selected from the group consisting of methoxy, ethoxy, iso-propoxy, n-propoxy, n-butoxy, iso-butoxy, cyclopentoxy, allyloxy, 4-methylpentoxy, —O—CH$_2$—(2,2-dimethyl-1,3-dioxolan-4-yl), —O—CH$_2$-cyclohexyl, —O—CH$_2$—(3-tetrahydrofuranyl), —O—CH$_2$—C(O)O-tert-butyl, —O—CH$_2$—C(CH$_3$)$_3$, and —OCH$_2$CH(CH$_2$CH$_3$)$_2$.

19. The compound according to claim 11 wherein the compound of formula I is selected from the group consisting of:

N-(3-trifluoromethyl-4-chlorophenyl)alanine ethyl ester;
N-(3,4-dichlorophenyl)alanine benzyl ester;
N-(3,4-dichlorophenyl)alanine cyclopentyl ester;
N-(3,4-dichlorophenyl)alanine allyl ester;
N-(3,4-dichlorophenyl)alanine 2,2-dimethyl-1,3-dioxolane-4-methyl ester;
N-(3,4-dichlorophenyl)alanine cyclohexylmethyl ester;
N-(3,4-dichlorophenyl)alanine tert-butoxycarbonylmethyl ester;
2-{N-(3,4-dichlorophenyl)amino}pentanoic acid iso-butyl ester;
N-(4-cyanophenyl)alanine iso-butyl ester;
N-(3-chloro-4-cyanophenyl)alanine iso-butyl ester;
N-(3,4-dichlorophenyl)alanine tetrahydrofuran-3-yl-methyl ester;
2-{N-(3,4-dichlorophenyl)amino}butanoic acid iso-butyl ester;
N-(4-ethylphenyl)alanine methyl ester;
N-{4-(1-ethoxy)ethylphenyl}alanine methyl ester;
N-(4-azidophenyl)alanine iso-butyl ester;
N-{(4-phenylcarbonyl)phenyl}alanine iso-butyl ester;
N-(3,4-dichlorophenyl)alanine O-acylacetamidoxime ester;
N-(3,4-dichlorophenyl)alanine pyrrolyl amide;
N-(3,4-dichlorophenyl)alanine O-acylpropionamideoxime ester;
N-(3,4-dichlorophenyl)alanine O-acylbutyramideoxime ester;
2-{N-(naphth-2-yl)amino}butanoic acid ethyl ester;

N-(naphth-2-yl)alanine iso-butyl ester;
N-(2-methylquinolin-6-yl)alanine iso-butyl ester;
N-(3,4-ethylenedioxyphenyl)alanine iso-butyl ester;
N-(3,4-methylenedioxyphenyl)alanine iso-butyl ester;
N-(naphth-2-yl)alanine methyl ester;
N-(benzothiazol-6-yl)alanine ethyl ester;
N-(indol-5-yl)alanine iso-butyl ester;
N-(naphth-2-yl)alanine O-acylacetamidoxime ester;
N-(4-ethoxycarbonylphenyl)alanine iso-butyl ester;
N-(3,5-di(trifluoromethyl)phenyl)alanine iso-butyl ester;
N-(3,5-dimethoxyphenyl)alanine iso-butyl ester;
N-(2-napthyl)alanine O-acylpropionamidoxime ester;
N-(2-napthyl)alanine O-acylbutyramidoxime ester;
N-(2-napthyl)alanine O-acylisovaleramidoxime ester;
N-(2-napthyl)alanine O-acylbenzamidoxime ester;
N-(2-napthyl)alanine O-acylcyclopropanecarboxamidoxime ester;
N-(2-napthyl)alanine O-acylcyclopropylacetamidoxime ester; and
N-(2-napthyl)alanine O-acylcyclopentanecarboxamidoxime ester.

20. A compound of formula III:

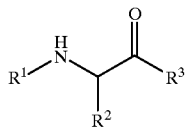

III wherein
  $R^1$ is selected from the group consisting of:
    (a) a substituted phenyl group of formula II:

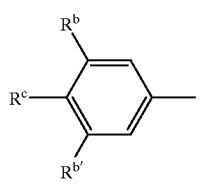

II wherein
  $R^c$ is selected from the group consisting of acyl, alkyl, alkoxy, alkoxycarbonyl, alkylalkoxy, azido, cyano, halo, hydrogen, nitro, trihalomethyl, thioalkoxy, and where $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
  $R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
    (b) 2-naphthyl; and
    (c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;
  $R^2$ is alkyl selected from the group consisting of ethyl, n-propyl, iso-propyl, n-butyl, and iso-butyl; and
  $R^3$ is selected from the group consisting of:
    (a) —Y(CH$_2$)$_n$CHR$^4$R$^5$ wherein n is an integer of from 0 to 2, Y is selected from the group consisting of oxygen and sulfur, $R^4$ and $R^5$ are independently selected from the group consisting of hydrogen, alkyl, alkenyl, aryl optionally substituted with from 1 to 3 substituents selected from the group consisting of alkyl, alkoxy, halo, cyano, nitro, trihalomethyl, and thioalkoxy, heteroaryl optionally substituted with from 1 to 3 substituents selected from the group consisting of alkyl, alkoxy, halo, cyano, nitro, trihalomethyl, and thioalkoxy, and where $R^4$ and $R^5$ are joined to form a cycloalkyl group, a cycloalkenyl group or a heterocyclic group;
    (b) —ON=C(NH$_2$)R$^6$ where $R^6$ is selected from the group consisting of alkyl, aryl, cycloalkyl, and heteroaryl;
    (c) —O(CH$_2$)$_p$C(O)OR$^7$ wherein p is an integer of from 1 to 2 and $R^7$ is alkyl;
    (d) —NR$^8$R$^9$ wherein $R^8$ and $R^9$ are joined to form a pyrrolyl group;
and pharmaceutically acceptable salts thereof.

* * * * *